United States Patent
Lee et al.

(10) Patent No.: US 12,059,312 B2
(45) Date of Patent: Aug. 13, 2024

(54) NEUROSURGICAL SYSTEMS AND RELATED METHODS

(71) Applicant: Mayo Foundation for Medical Education and Research, Rochester, MN (US)

(72) Inventors: Kendall H. Lee, Rochester, MN (US); Stephan J. Goerss, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1042 days.

(21) Appl. No.: 16/966,185

(22) PCT Filed: Feb. 6, 2019

(86) PCT No.: PCT/US2019/016873
§ 371 (c)(1),
(2) Date: Jul. 30, 2020

(87) PCT Pub. No.: WO2019/157070
PCT Pub. Date: Aug. 15, 2019

(65) Prior Publication Data
US 2021/0038338 A1 Feb. 11, 2021

Related U.S. Application Data

(60) Provisional application No. 62/627,520, filed on Feb. 7, 2018.

(51) Int. Cl.
*A61B 90/11* (2016.01)
*A61B 90/14* (2016.01)
*A61B 34/20* (2016.01)

(52) U.S. Cl.
CPC .............. *A61B 90/11* (2016.02); *A61B 90/14* (2016.02); *A61B 2034/2065* (2016.02)

(58) Field of Classification Search
CPC ......... A61B 90/14; A61B 90/11; A61B 90/10; A61B 17/17; A61B 17/1728; A61B 2034/2065
See application file for complete search history.

(56) References Cited

U.S. PATENT DOCUMENTS 5,163,430 A * 11/1992 Carol .................... A61B 90/11
378/20
6,546,277 B1 8/2003 Franck et al.
(Continued)

FOREIGN PATENT DOCUMENTS

| CN | 103140185 | 6/2013 |
| CN | 108124421 | 6/2018 |

(Continued)

OTHER PUBLICATIONS

Abosch et al., "An assessment of current brain targets for deep brain stimulation surgery with susceptibility-weighted imaging at 7 tesla," Neurosurgery, Dec. 2010, 67(6):1745-1756.
(Continued)

*Primary Examiner* — Kathleen S Holwerda
*Assistant Examiner* — Daniel Icet
(74) *Attorney, Agent, or Firm* — Fish & Richardson P.C.

(57) ABSTRACT

A surgical system includes a skull attachment device that includes a support base configured to seat against a skull of a patient and one or more pins extending from a bottom surface of the support base and configured to pierce the scalp to seat the skull attachment device against the skull. The surgical system also includes an interface disposed along a top surface of the support base and having a shape that compliments a profile of a mating feature of a stereotactic
(Continued)

device for defining a position and an orientation of the stereotactic device with respect to the support base while the interface is engaged with the mating feature.

14 Claims, 29 Drawing Sheets

(56) References Cited

U.S. PATENT DOCUMENTS

| | | | |
|---|---|---|---|
| 6,738,657 | B1 | 5/2004 | Franklin et al. |
| 7,559,935 | B2 * | 7/2009 | Solar ............... A61B 90/11 606/130 |
| 7,896,889 | B2 | 3/2011 | Mazzocchi et al. |
| 7,925,328 | B2 | 4/2011 | Urquhart et al. |
| 8,298,245 | B2 | 10/2012 | Li et al. |
| 9,192,446 | B2 | 11/2015 | Piferi et al. |
| 9,289,270 | B2 | 3/2016 | Gielen et al. |
| 2004/0167543 | A1 | 8/2004 | Mazzocchi et al. |
| 2009/0112084 | A1 * | 4/2009 | Piferi ............... A61N 1/0529 600/421 |
| 2011/0092771 | A1 | 4/2011 | Hynes |
| 2012/0060847 | A1 | 3/2012 | Stratton et al. |
| 2013/0211424 | A1 | 8/2013 | Thiran et al. |
| 2014/0066750 | A1 * | 3/2014 | Piferi ............... A61B 90/11 600/417 |
| 2016/0113719 | A1 | 4/2016 | Stratton et al. |
| 2018/0110568 | A1 | 4/2018 | Lenarz et al. |

FOREIGN PATENT DOCUMENTS

| | | |
|---|---|---|
| DE | 202007000748 | 4/2007 |
| DE | 102016205210 | 10/2017 |
| JP | S61-73308 | 5/1986 |
| JP | H3-10969 | 3/1991 |
| JP | H5-84309 | 11/1993 |
| JP | 2016-077356 | 5/2016 |

OTHER PUBLICATIONS

Alba-Ferrara et al., "Transcranial Magnetic Stimulation and Deep Brain Stimulation in the treatment of alcohol dependence," Addict. Disord. Their Treatment, Dec. 2014, 13(4):159-169.
Balachandran et al., "Accuracy Evaluation of microTargeting Platforms for Deep-Brain Stimulation Using Virtual Targets," IEEE Trans. Biomed. Engineering, Jan. 2009, 56(1):37-44.
Bartsch et al., "Deep brain stimulation for addiction, anorexia and compulsion. Rationale, clinical results and ethical implications," Neurologist, Feb. 2014, 85(2):162-168 (with Machine Translation).
Benabid et al., "Combined (Thalamotomy and Stimulation) Stereotactic Surgery of the VIM Thalamic Nucleus for Bilateral Parkinson Disease," Appl. Neurophysiology, 1987, 50(1-6):344-346.
Ben-Haim et al., "Evaluation of Patient Perspectives Toward Awake, Frame-Based Deep-Brain Stimulation Surgery," World Neurosurgery, Mar. 2018, 111:e601-e607.
Ben-Haim et al., "Risk Factors for Hemorrhage During Microelectrode-Guided Deep Brain Stimulation and the Introduction of an Improved Microelectrode Design," Neurosurgery, Apr. 2009, 64(4):754-763.
Berkowitz et al., "Pullout Strength of Self-Tapping Screws Inserted to Different Depths," J. Orthop. Trauma, Aug. 2005, 19(7):462-465.
Bewernick et al., "Deep brain stimulation to the medial forebrain bundle for depression-long-term outcomes and a novel data analysis strategy," Brain Stimulation, May 1, 2017, 10(3):664-671.
Bick et al., "Neuromodulation for restoring memory," Neurosurg. Focus, May 2016, 40(5):E5, 12 pages.
Bjartmarz et al., "Comparison of Accuracy and Precision between Frame-Based and Frameless Stereotactic Navigation for Deep Brain Stimulation Electrode Implantation," Stereotact. Funct: Neurosurgery, May 25, 2007, 85(5):235-242.
Bot et al., "Analysis of Stereotactic Accuracy in Patients Undergoing Deep Brain Stimulation Using Nexframe and the Leksell Frame," Stereotact. Funct. Neurosurgery, Jul. 29, 2015, 93(5):316-325.

Chabardes et al., "Surgical implantation of STN-DBS leads using intraoperative MRI guidance: technique accuracy and clinical benefit at 1-year follow-up," Acta Neurochirurgica, Apr. 2015, 157(4):729-737.
Chen et al., "Complication rates, lengths of stay, and readmission rates in "awake" and "asleep" deep brain simulation," J. Neurosurgery, Aug. 2017, 127(2):360-369.
Cho et al., "Direct visualization of deep brain stimulation targets in Parkinson disease with the use of 7-tesla magnetic resonance imaging," J. Neurosurgery, Sep. 2010, 113(3):639-647.
Clarke et al., "On a Method of Investigating the Deep Ganglia and Tracts of the Central Nervous System (Cerebellum)," Br. Med. Journal, Oct. 2007, 1906:1799-1800.
Dandy, "Ventriculography Following the Injection of Air into the Cerebral Ventricles," Ann. Surgery, Jul. 1918. 68(1):5-11.
Deuschl et al., "A Randomized Trial of Deep-Brain Stimulation for Parkinson's Disease," N. Engl. J. Medicine, Aug. 31, 2006, 355(9):896-908.
Deuschl et al., "Treatment of patients with essential tremor," Lancet Neurology, Feb. 2011, 10(2):148-161.
Dougherty et al., "A Randomized Sham-Controlled Trial of Deep Brain Stimulation of the Ventral Capsule/Ventral Striatum for Chronic Treatment-Resistant Depression," Biol. Psychiatry, Aug. 2015, 78(4):240-248.
Duchin et al., "Feasibility of Using Ultra-High Field (7 T) MRI for Clinical Surgical Targeting," PLoS One, May 17, 2012, 7(5):e37328, 10 pages.
Edwards et al., "Neurostimulation Devices for the Treatment of Neurologie Disorders," Mayo Clin. Proceedings, Sep. 1, 2017, 92(9):1427-1444.
Edwards et al., "A novel re-attachable stereotactic frame for MRI-guided neuronavigation and its validation in a large animal and human cadaver model," J. Neural Eng., Sep. 2018, 15(6):066003, 12 pages.
Faria et al., "Review of Robotic Technology for Stereotactic Neurosurgery," IEEE Rev. Biomed. Engineering, Apr. 2015, 8:125-137.
Fedorov et al., "3D Slicer as an image computing platform for the Quantitative Imaging Network," Magn. Reson. Imaging, Nov. 2012, 30(9):1323-1341.
Felix et al., "Stereotaxic atlas of the pig brain," Brain Res. Bulletin, May 1999, 49(1-2):1-137.
Fitzpatrick, "The role of registration in accurate surgical guidance;" Proc. Inst. Mech. Engineers, May 2010, 224(5):607-622.
Follett et al., "Pallidal versus Subthalamic Deep-Brain Stimulation for Parkinson's Disease," N. Engl. J. Medicine, Jun. 3, 2010, 362(22):2077-2091.
Gibson et al., "Anterior Thalamic Deep Brain Stimulation: Functional Activation Patterns in a Large Animal Model," Brain Stimulation, Sep. 2016, 9(5):770-773.
Goerss et al., "A Computed Tomographic Stereotactic Adaptation System," Neurosurgery, Mar. 1982, 10(3):375-379.
Goerss et al., "Automated stereotactic positioning system," Appl. Neurophysiology, 1987, 50(1-6):100-106.
Goodman et al., "Deep Brain Stimulation for Intractable Obsessive Compulsive Disorder: Pilot Study Using a Blinded, Staggered-Onset Design," Biol. Psychiatry, Mar. 15, 2010, 67(6):535-542.
Gorny et al., "Measurements of RF heating during 3.0-T MRI of a pig implanted with deep brain stimulator," Magn. Reson. Imaging, Jun. 2013, 31(5):783-788.
Grahn et al., "MRI-Guided Stereotactic System for Delivery of Intraspinal Microstimulation," Spine, Jul. 2016, 41(13):E806-813.
Hertel et al., "Implantation of Electrodes for Deep Brain Stimulation of the Subthalamic Nucleus in Advanced Parkinson's Disease with the Aid of Intraoperative Microrecording Under General Anesthesia," Neurosurgery, Nov. 2006, 59(5):E1138, 8 pages.
Ho et al., "Awake versus asleep deep brain stimulation for Parkinson's disease: a critical comparison and meta-analysis," J. Neurol. Neurosurg. Psychiatry, Mar. 1, 2017, 89(7):687-691.
Honey et al., "Deep Brain Stimulation Target Selection for Parkinson's Disease," Can. J. Neurol. Sciences, Jan. 2017, 44(1):3-8.
Huang et al., "Characteristics of local field potentials correlate with pain relief by deep brain stimulation," Clin. Neurophysiology, Jul. 2016, 127(7):2573-2580.

(56) References Cited

OTHER PUBLICATIONS

Hyam et al., "Implementing novel trial methods to evaluate surgery for essential tremor," Br. J. Neurosurgery, May 2015, 29(3):334-339.
Kalia et al., "Deep brain stimulation for Parkinson's disease and other movement disorders," Curr. Opin. Neurology, Aug. 2013, 26(4):374-380.
Kelly et al., "Computer Simulation for the Stereotactic Placement of Interstitial Radionuclide Sources into Computed Tomography-defined Tumor Volumes," Neurosurgery, Apr. 1984, 14(4):442-448.
Kelly et al., "Magnetic Resonance Imaging-Based Computer-Assisted Stereotactic Resection of the Hippocampus and Amygdala in Patients With Temporal Lobe Epilepsy," Mayo Clinic Proceedings, Feb. 1987, 62(2):103-108.
Knight et al., "Nucleus Accumbens Deep Brain Stimulation Results in Insula and Prefrontal Activation: A Large Animal fMRI Study," PLoS One, Feb. 2013, 8(2):e56640, 10 pages.
Konrad et al., "Customized, Miniature Rapid-Prototype Stereotactic Frames for Use in Deep Brain Stimulator Surgery: Initial Clinical Methodology and Experience from 263 Patients from 2002 to 2008," Stereotact. Funct. Neurosurgery, Dec. 15, 2010, 89(1):34-41.
Krack et al., "Five-Year Follow-up of Bilateral Stimulation of the Subthalamic Nucleus in Advanced Parkinson's Disease," N. Engl. J. Medicine, Nov. 13, 2003, 349(20):1925-1934.
Kratchman, "Image-Guided Targeting and Control of Implantable Electrodes," Dissertation for the degree of Doctor of Philosophy, Vanderbilt University, May 2015, 156 pages.
Kupsch et al., "Pallidal Deep-Brain Stimulation in Primary Generalized or Segmental Dystonia," N. Engl. J. Medicine, Nov. 9, 2006, 355(19):1978-1990.
Laxton et al., "Deep brain stimulation for the treatment of Alzheimer disease and dementias," World Neurosurgery, Sep./Oct. 2013, 80(3-4):S28.E1-E8.
Lempka et al., "Randomized clinical trial of deep brain stimulation for post-stroke pain," Ann. Neurology, May 2017, 81(5):653-663.
Lenglet et al., "Comprehensive in vivo Mapping of the Human Basal Ganglia and Thalamic Connectome in Individuals Using 7T MRI," PLoS One, Jan. 3, 2012, 7(1):e29153, 14 pages.
Machado et al., "Deep Brain Stimulation for Parkinson's Disease: Surgical Technique and Perioperative Management," Mov. Disorders, Jun. 2006, 21(S14):S247-258.
Mascott et al., "Quantification of True In Vivo (Application) Accuracy in Cranial Image-guided Surgery: Influence of Mode of Patient Registration," Neurosurgery, Jul. 2006, 59(ONS1):ONS146-156.
Maurer et al., "Registration of Head Volume Images Using Implantable Fiducial Markers," IEEE Trans. Med. Imaging, Aug. 1997, 16(4):447-462.
Metzger et al., "Comparison of 4 registration strategies for computer-aided maxillofacial surgery," Otolaryngol. Head Neck Surgery, Jul. 2007, 137(1):93-99.
Min et al., "Deep brain stimulation induces BOLD activation in motor and non-motor networks: an fMRI comparison study of STN and EN/GPi DBS in large animals," NeuroImage, Nov. 2012, 63(3):1408-1420.
Min et al., "Subthalamic Nucleus Deep Brain Stimulation Induces Motor Network BOLD Activation: Use of a High Precision MRI Guided Stereotactic System for Nonhuman Primates," Brain Stimulation, Jul. 2014, 7(4):603-607.
Mirzadeh et al., "Validation of CT-MRI Fusion for Intraoperative Assessment of Stereotactic Accuracy in DBS Surgery," Mov: Disorders, Dec. 2014, 29(14):1788-1795.
Mundinger et al., "CT Stereotactic Biopsy for Optimizing the Therapy of Intracranial Processes," Acta Neurochirurgica, 1985, Suppl. 35:70-74.
Mundinger et al., "New stereotactic treatment of spasmodic torticollis with a brain stimulation system," Med. Klinik, Nov. 1977, 72(46):1982-1986 (with Machine Translation).
Nakazawa et al., "Geometric accuracy of 3D coordinates of the Leksell stereotactic skull frame in 1.5 Tesla- and 3.0 Tesla-magnetic resonance imaging: a comparison of three different fixation screw materials," J. Radiat. Research, Nov. 2014, 55(6):1184-1191.
Neumann et al., "Spatial Distortion in MRI-Guided Stereotactic Procedures: Evaluation in 1.5-, 3- and 7 Tesla MRI Scanners," Stereotact. Funct. Neurosurgery, Dec. 16, 2015, 93(6):380-386.
Okun et al., "Identifying candidates for deep brain stimulation in Parkinson's disease: the role of the primary care physician," Geriatrics, May 2007, 62(5):18-24.
Ostertag et al., "Stereotactic biopsy of brain tumors," Surg. Neurology, Oct. 1980, 14(4):275-283.
Ostrem et al, "Clinical outcomes using ClearPoint interventional MRI for deep brain stimulation lead placement in Parkinson's disease," J. Neurosurgery, Apr. 2016, 124(4):908-916.
Owen et al., "Frame-based stereotaxy in a frameless era: current capabilities, relative role, and the positive- and negative predictive values of blood through the needle," J. Neuro-Oncology, May 2009, 93(1):139-149.
Paek et al., "Frequency-dependent functional neuromodulatory effects on the motor network by ventral lateral thalamic deep brain stimulation in swine," NeuroImage, Jan. 2015, 105:181-188.
PCT International Preliminary Report on Patentability in International Appln. No. PCT/US2019/016873, dated Aug. 11, 2020, 7 pages.
PCT International Search Report and Written Opinion in International Appln. No. PCT/US2019/016873, dated May 2, 2019, 9 pages.
Picard et al., "The first human stereotaxic apparatus. The contribution of Aubrey Mussen to the field of stereotaxis," J Neurosurgery, Oct. 1983, 59(4):673-676.
Pierce et al., "Deep brain stimulation for the treatment of addiction: basic and clinical studies and potential mechanisms of action," Psychopharmacology, Oct. 2013, 229(3):487-491.
Plantinga et al., "Individualized parcellation of the subthalamic nucleus in patients with Parkinson's disease with 7T MRI," Neuroimage, Sep. 26, 2016, 168:403-411.
Plantinga et al., "Ultra-high field magnetic resonance imaging of the basal ganglia and related structures," Front. Hum. Neuroscience, Nov. 5, 2014, 8:876, 22 pages.
Plantinga et al., "Ultra-High Field MRI Post Mortem Structural Connectivity of the Human Subthalamic Nucles, Substantia Nigra, and Globus Pallidus," Front. Neurology, Jun. 16, 2016, 10:66, 10 pages.
Poon et al., "Anaesthesia for deep brain stimulation and in patients with implanted neurostimulator devices," Br. J. Anaesthesia, Aug. 1, 2009, 103(2):152-165.
Riechert et al., "A new stereotactic instrument for intracranial placement of electrodes," Arch. Psychiatr. Nervenkr. Z. Gesamte. Neurol. Psychiatrie, 1951, 186(2):225-230 (with Machine Translation).
Rusheen et al., "A compact stereotactic system for image-guided surgical intervention," J. Neural Engineering, Dec. 16, 2020, 17(6):066014, 13 pages.
Sakamoto et al., "Assessment of the RIVET fixation system for cranioplasty using the pull-out technique," J. Craniomaxillofac. Surgery, Mar. 2015, 43(2):281-284.
Schuepbach et al., "Neurostimulation for Parkinson's Disease with Early Motor Complications," N. Engl. J. Medicine, Feb. 14, 2013, 368(7):610-622.
Segar et al., "Deep brain stimulation for the obsessive-compulsive and Tourette-like symptoms of Kleefstra syndrome," Neurosurg. Focus, Jun. 2015, 38(6):E12, 5 pages.
Seibert et al., "Distortion inherent to magnetic resonance imaging can lead to geometric miss in radiosurgery planning," Pract. Radiat. Oncology, Nov. 2016, 6(6):e319-328.
Servello et al., "Deep Brain Stimulation in Gilles de la Tourette Syndrome: What Does the Future Hold? A Cohort of 48 Patients," Neurosurgery, Jan. 2016, 78(1):91-100.
Settell et al., "Functional Circuitry Effect of Ventral Tegmental Area Deep Brain Stimulation: Imaging and Neurochemical Evidence of Mesocortical and Mesolimbic Pathway Modulation," Front. Neuroscience, Mar. 3, 2017, 11:104, 11 pages.
Shen et al., "Neuroscience: Tuning the Brain," Nature, Mar. 2014, 507(7492):290-292.

(56) References Cited

OTHER PUBLICATIONS

Sillay et al., "Perioperative Brain Shift and Deep Brain Stimulating Electrode Deformation Analysis: Implications for rigid and non-rigid devices," Ann. Biomed. Engineering, Feb. 2013, 41(2):293-304.
Sims-Williams et al., "Characterising the Analgesic Effect of Different Targets for Deep Brain Stimulation in Trigeminal Anaesthesia Dolorosa," Stereotact. Funct. Neurosurgery, Jun. 21, 2016, 94(3):174-181.
Sironi, "Origin and evolution of deep brain stimulation," Front. Integr. Neuroscience, Aug. 18, 2011, 5:42, 5 pages.
Smeets et al., "Thalamic Deep Brain Stimulation for Refractory Tourette Syndrome: Clinical Evidence for Increasing Disbalance of Therapeutic Effects and Side Effects at Long-Term Follow-Up," Neuromodulation, Jan. 19, 2017, 21(2):197-202.
Spiegel et al., "Stereotaxic Apparatus for Operations on the Human Brain," Science, Oct. 1947, 106(2754):349-350.
Starr et al., "Subthalamic nucleus deep brain stimulator placement using high-field interventional magnetic resonance imaging and a skull-mounted aiming device: technique and application accuracy," J. Neurosurgery, Mar. 2010, 112(3):479-490.
Testini et al., "Deep Brain Stimulation for Tourette's Syndrome: The Case for Targeting the Thalamic Centromedian-Parafascicular Complex," Front. Neurology, Nov. 10, 2016, 7:193, 9 pages.
Toyoda et al., "The Effectiveness of the Stereotactic Burr Hole Technique for Deep Brain Stimulation," Neurol. Med. Chirurgica, Sep. 2015, 55(9):766-772.
Tsolaki et al., "Using probabilistic tractography to target the subcallosal cingulate cortex in patients with treatment resistant depression," Psychiatry Res. Neuroimaging, Jan. 20, 2017, 261:72-74.
Vidailhet et al., "Bilateral Deep-Brain Stimulation of the Globus Pallidus in Primary Generalized Dystonia," N. Engl. J. Medicine, Feb. 3, 2005, 352(5):459-467.
Vidailhet et al., "Bilateral, pallidal, deep-brain stimulation in primary generalised dystonia: a prospective 3 year follow-up study," Lancet Neurology, Mar. 2007, 6(3):223-229.
Walton et al., "A Phantom Study to Assess the Accuracy of Stereotactic Localization, Using T1-weighted Magnetic Resonance Imaging with the Leksell Stereotactic System," Neurosurgery, Jan. 1996, 38(1):170-176.
Walton et al., "Development of a relocatable frame technique for gamma knife radiosurgery. Technical note," J. Neurosurgery, Dec. 2000, 93(Suppl. 3):198-202.
Wang et al., "Pain experience using conventional versus angled anterior posts during stereotactic head frame placement for radiosurgery," J. Clin. Neuroscience, Sep. 2014, 21(9):1538-1542.
Weaver et al., "Bilateral Deep Brain Stimulation vs Best Medical Therapy for Patients With Advanced Parkinson Disease: A Randomized Controlled Trial," JAMA, Jan. 7, 2009, 301(1):63-73.
Xu et al., "Deep Brain Stimulation for Alzheimer's Disease," Curr. Alzheimer Research, 2017, 14(4):356-361.
Zesiewicz et al., "Evidence-based guideline update: treatment of essential tremor: Report of the Quality Standards Subcommittee of the American Academy of Neurology," Neurology, Nov. 2011, 77(19):1752-1755.

* cited by examiner

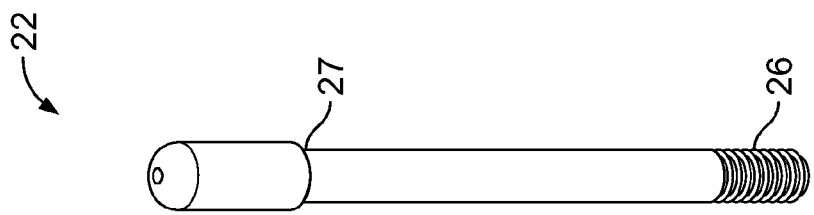
FIG. 12
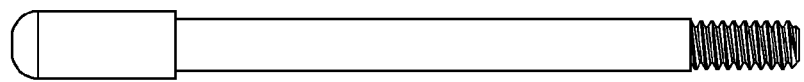
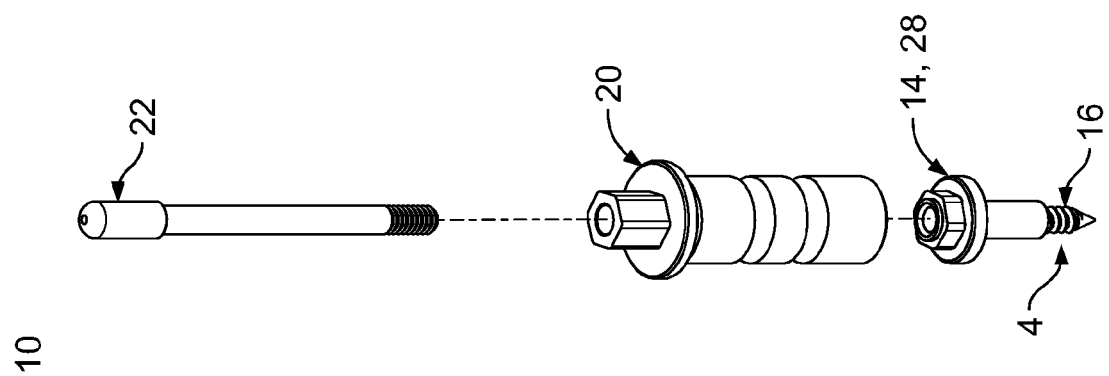
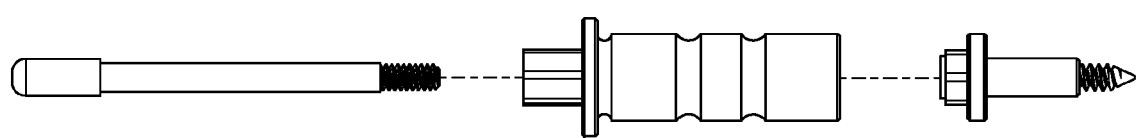
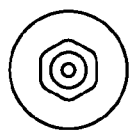 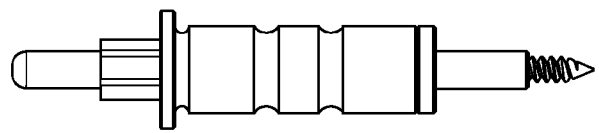
FIG. 11

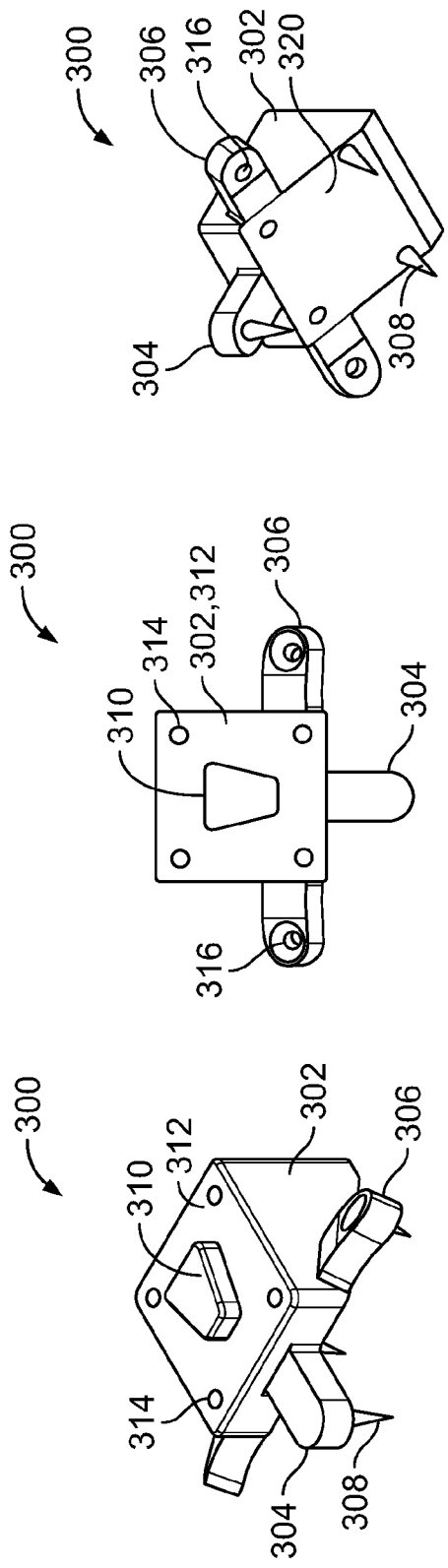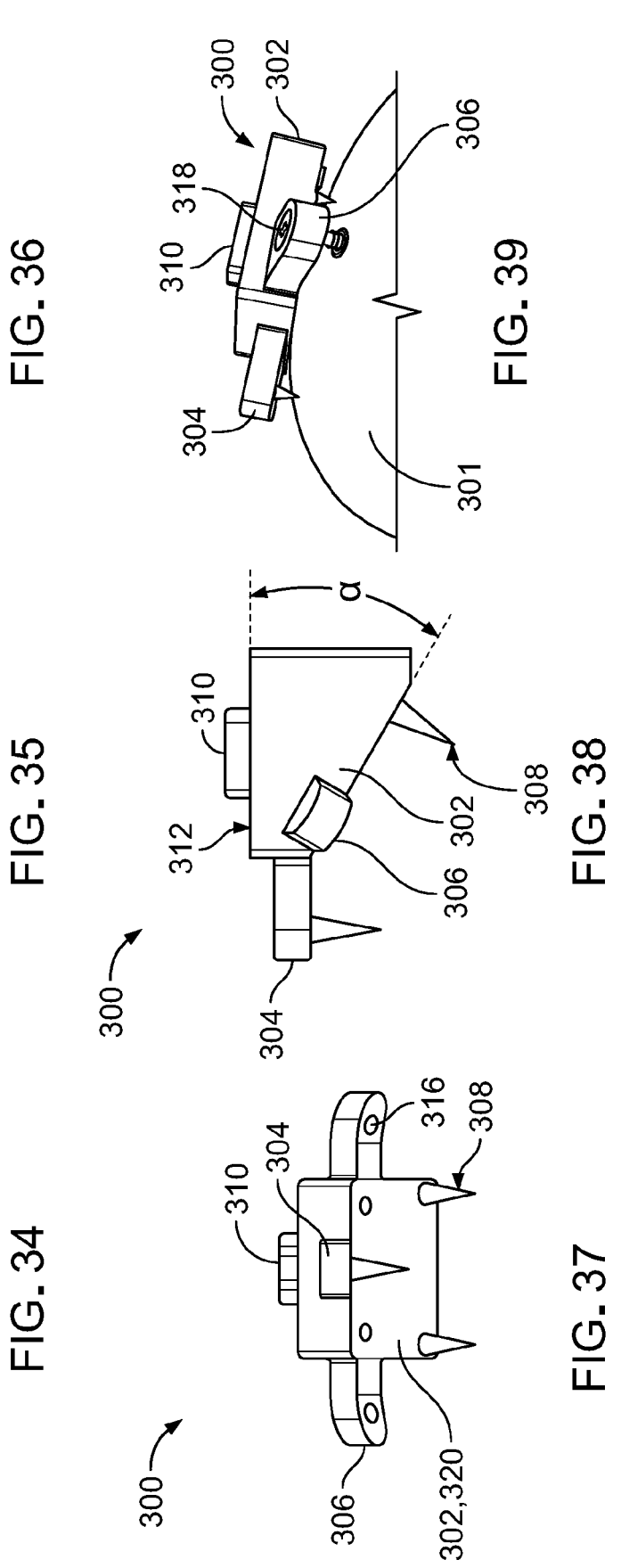

Solid Mechanical

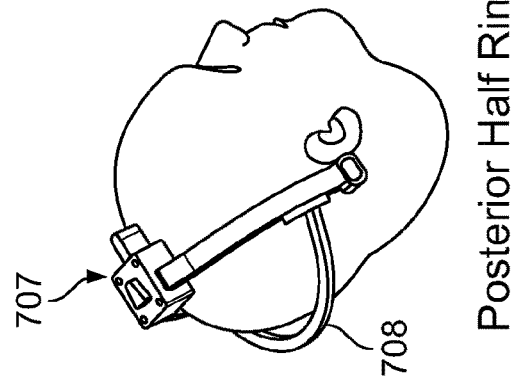
FIG. 55
Pivot Mechanism
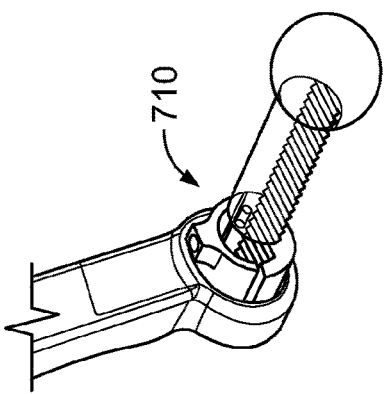
FIG. 56
Posterior Half Ring
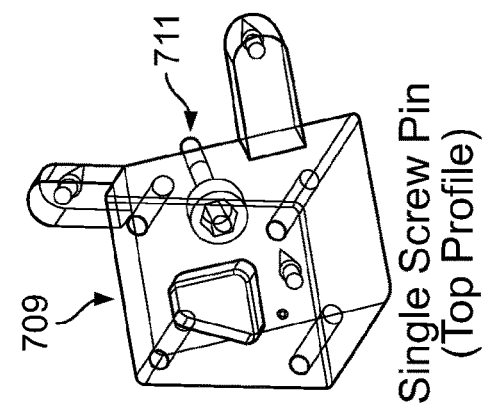
FIG. 58
Single Screw Pin
(Top Profile)
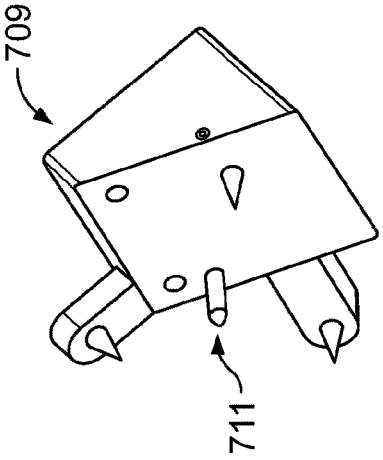
FIG. 57
Single Screw Pin
Bottom Profile
FIG. 59
Rachet Pin Mechanism

NEUROSURGICAL SYSTEMS AND RELATED METHODS

CROSS REFERENCE TO RELATED APPLICATIONS

This application is a National Stage application under 35 U.S.C. § 371 of International Application No. PCT/US2019/016873, having an International Filing Date of Feb. 6, 2019, which claims priority to U.S. Provisional Patent Application No. 62/627,520, filed on Feb. 7, 2018, the entire contents of which are incorporated herein by reference.

TECHNICAL FIELD

This disclosure relates to neurosurgical systems, and more particularly to stereotactic device components and related surgical procedures.

BACKGROUND

Deep brain stimulation (DBS) surgery can be performed using stereotactic devices and typically involves two phases that are taxing on time, equipment, and personnel resources. The first stage involves image acquisition and surgical planning. During the first stage, a patient's head is immobilized in a stereotactic headframe, planning magnetic resonance (MR) and/or computed tomography (CT) examinations are performed, and a surgical plan is created to access one or more targets within the brain using a surgical planning tool, such as a computer program. The patient is generally awake during the first stage and experiences discomfort from the headframe. During the second stage of the surgery, the patient is transported to an operating room (OR) so that the stereotactic procedure can be performed on the patient using the surgical plan. To perform the procedure, a stereotactic device is attached to the headframe, and values determined by the surgical plan are applied to the stereotactic device. The values include Cartesian coordinates (e.g., x, y, z) and angles. Electrodes are attached to an adjustable component of the stereotactic device and delivered to the targets according to the values of the surgical plan. The lengthiness and intricacy of the process is taxing on both the patient, physician and OR resources.

SUMMARY

The present disclosure relates to surgical systems that can decouple an imaging and planning stage of a neurosurgical procedure from a plan execution stage of the neurosurgical procedure, thereby reducing an amount of time needed in an operating room (OR) and associated equipment and personnel resources needed to carry out the procedure. Examples of such surgical procedures include deep brain stimulation, electrophysiology, external ventricular drain, and other techniques.

In one aspect, a surgical system includes anchor screws configured to attach to a bone structure, a template defining an arrangement that locates the anchor screws in fixed positions relative to each other, and a surgical frame including connection points defined in the arrangement such that the connection points can be collocated with the anchor screws. The surgical frame is reversibly connectable to the anchor screws.

Embodiments may include the following features.

In some embodiments, the surgical system further includes standoffs that can reversibly attach to the anchor screws.

In certain embodiments, the standoffs include a ball construction.

In some embodiments, the standoffs include a cylindrical construction.

In certain embodiments, the standoffs include a V-shaped edge.

In some embodiments, the surgical system further includes arms that are configured to connect the standoffs to the surgical frame.

In certain embodiments, the surgical system further includes arms that are configured to connect the anchor screws to the surgical frame.

In some embodiments, the anchor screws include self-tapping screw tips that are configured to be positioned subcutaneously.

In certain embodiments, the anchor screws include anchor bodies that are configured to be secured to the bone structure.

In some embodiments, the anchor screws include two anchor screws.

In some embodiments, the anchor screws include three anchor screws.

In certain embodiments, the anchor screws include four anchor screws.

In some embodiments, the anchor screws include more than four anchor screws.

In certain embodiments, the anchor screws are configured to attach to a skull.

In some embodiments, the surgical frame includes an imaging frame.

In certain embodiments, the surgical system further includes a stereotactic device that includes the surgical frame.

In some embodiments, the stereotactic device includes an instrument guide.

In certain embodiments, the stereotactic device provides five degrees of freedom by which the instrument guide can be adjusted.

In some embodiments, the degrees of freedom include linear degrees of freedom and angular degrees of freedom.

In certain embodiments, the stereotactic device is configured to be adjusted manually.

In some embodiments, the stereotactic device is configured to be adjusted in an automated manner.

In certain embodiments, the stereotactic device defines a cylindrical work envelope.

In some embodiments, the stereotactic device is configured to operate with 7.0T MRI.

In certain embodiments, the surgical frame is a first surgical frame and the connection points are first connection points, the surgical system further including a second surgical frame including second connection points defined in the arrangement such that the second connection points can be collocated with the anchor screws, the second surgical frame being reversibly attachable to the anchor screws.

In some embodiments, image-guided frame-based stereotactic systems may include skull fixation components, a three-dimensional (3D) positioner, image localization components, and surgical planning software.

In certain embodiments, the skull fixation components include skull anchor screws for anchoring the stereotactic device to a cranium of a patient or a large laboratory animal, as well as other instruments and devices for implanting the anchor screws. A screw placement template can be used to implant the skull anchor screws (e.g., four skull anchor screws) in a precise pattern on the skull. In some embodiments, instruments used with the template include four sharpened rods to stabilize the template during screw implantation. Each sharpened rod is sequentially replaced with a drill guide that is used to create the precise hole pattern in the skull for the anchor screws. A tap matching the screw thread of the skull anchor screws is directed by the template to create threads in the holes. A driver that captivates a skull anchor screw is inserted into the template and advanced into the tapped holes. The template locks onto the driver to secure the template in place.

In certain embodiments, the skull anchor screws are made of titanium, polyether ether ketone (PEEK), sapphire, fused quartz, or stainless steel. In some examples, PEEK is optimal for magnetic resonance imaging (MRI) compatibility. The body of each skull anchor screw has a thread matching the tapped holes in skull. The tops of the skull anchor screws have a hex flange. Each skull anchor screw is advanced into the threaded hole until the flange abuts the skull. The hex top is used to drive the skull anchor screw into place. A threaded hole in the top of the skull anchor screw is used to attach the various devices of the stereotactic system to the skull.

In some embodiments, the stereotactic positioner has a rectangular base with multiple (e.g., four) supports extending toward a center of the stereotactic positioner. The supports are the connection site to the skull anchor screws implanted into the skull. In certain embodiments, Y axis rails are incorporated onto the base. A 3D slide attaches onto the Y axis rails. The 3D slide allows translation of the positioner about the skull to adjust to a location of the surgical target. The translation moves the arc quadrant, which functions to direct the surgical instruments and electrodes to the target. The arc quadrant has two degrees of freedom to alter the angular projection of the instrument to that target.

In certain embodiments, the image localizer attaches to the skull anchors screws. The image localizer functions to generate reference marks on images in known physical location with respect to the stereotactic positioner, allowing translation of image space into physical space.

In another aspect, a surgical system includes a skull attachment device that includes a support base configured to seat against a skull of a patient and one or more pins extending from a bottom surface of the support base and configured to pierce the scalp to seat the skull attachment device against the skull. The surgical system also includes an interface disposed along a top surface of the support base and having a shape that compliments a profile of a mating feature of a stereotactic device for defining a position and an orientation of the stereotactic device with respect to the support base while the interface is engaged with the mating feature.

Embodiments may include one or more of the following features.

In some embodiments, the top and bottom surfaces of the support base together define an angle in a range of about 0 degrees to about 40 degrees.

In certain embodiments, the skull attachment device further comprises lateral protrusions extending form the support base and respectively defining holes through which anchor screws can be passed to attach the skull attachment device to the skull.

In certain embodiments, the support base includes one or more features at which the support base can be attached to the stereotactic device.

In some embodiments, the interface protrudes from the top surface of the support base.

In certain embodiments, the interface is radially asymmetric.

In some embodiments, the top surface of the support base defines a plane including an origin of a stereotactic coordinate system while the skull attachment device is seated against the skull.

In certain embodiments, the surgical system further includes the stereotactic device.

In some embodiments, the stereotactic device includes an image localizer.

In certain embodiments, the stereotactic device includes an instrument guide.

In some embodiments, the stereotactic device is adjustable in three linear degrees of freedom and is adjustable in two or more rotational degrees of freedom for guiding an instrument to a target point located in a brain of the patient.

In certain embodiments, the stereotactic device includes an X axis carrier that is movable along an X axis rail, a Y axis carrier that is movable along a Y axis rail, a Z axis carrier that is movable along a Z axis rail, a collar angle carrier that is movable along a collar angle rail, and an arc angle carrier that is movable along an arc angle rail.

In some embodiments, the X axis rail is mounted to the collar angle carrier, and wherein the arc angle rail is mounted to the X axis carrier.

In certain embodiments, the collar angle carrier and the arc angle carrier together define a sphere having a center point that is coincident with the target point in the brain of the patient.

In some embodiments, the collar angle carrier and the arc angle carrier are orthogonal to each other.

In certain embodiments, the collar angle rail has a radius of curvature of about 160 mm to about 190 mm, and wherein the arc angle rail has a radius of curvature of about 160 mm to about 190 mm.

In some embodiments, the Z axis rail is rotatable about its own axis.

In certain embodiments, the surgical system further includes an imaging reference tool configured to be attached to the stereotactic device for verifying accurate placement of the instrument at the target point.

In some embodiments, the imaging reference tool includes a cross-hair reticle and a circle disposed on opposite sides of the imaging reference tool.

In certain embodiments, the stereotactic device is a first stereotactic device and the mating feature is a first mating feature, the surgical system further including a second stereotactic device having a second mating feature with the profile of the first mating feature.

DESCRIPTION OF DRAWINGS

FIGS. 1-5.

FIGS. 1-5.

FIG. 11 illustrates various views of a driver assembly of the template of FIGS. 1-5 together with the anchor screws of FIGS. 1-5.

FIG. 12 illustrates various views of a retaining rod of the driver assembly of FIG. 11.

FIGS. 34-38 illustrate various views of a skull attachment device.

FIG. 39 illustrates a skull attachment device attached to a skull of a patient.

FIGS. 54-59 illustrate various embodiments of alternative attachment of a skull attachment device to a skull.

Like reference symbols in the various figures indicate like elements. In some examples, illustrations shown in the drawings may not be drawn to scale.

DETAILED DESCRIPTION

Figure 3:
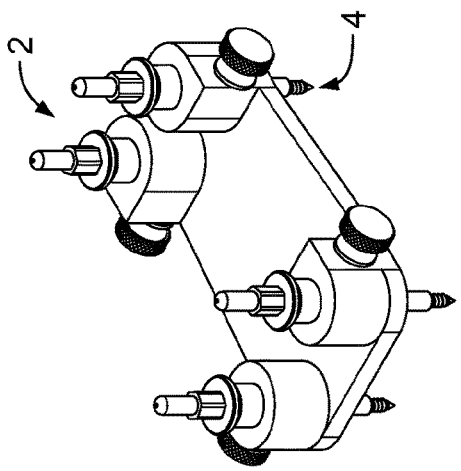
FIGS. 1-5 illustrate various view of a template for positioning anchor screws.
Figure 5:
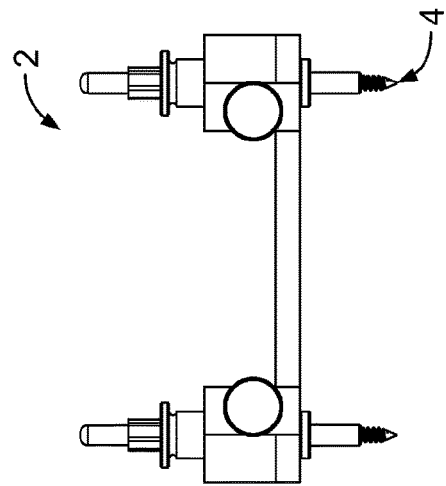
Figure 2:
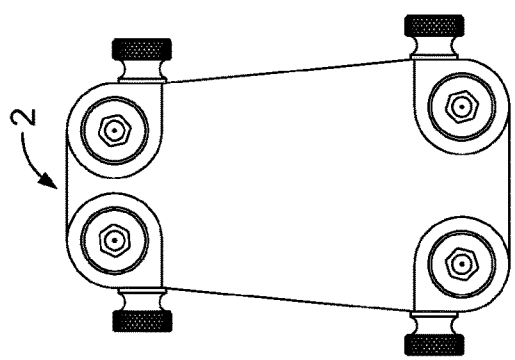
Figure 4:
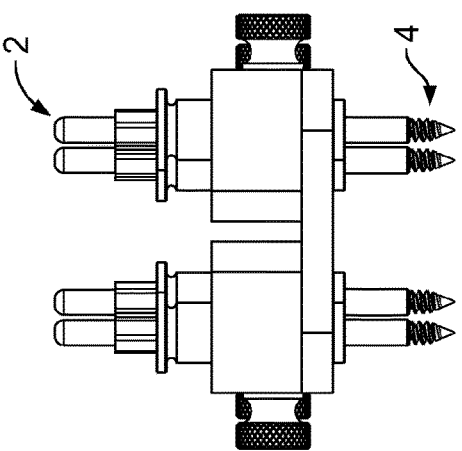
Figure 1:
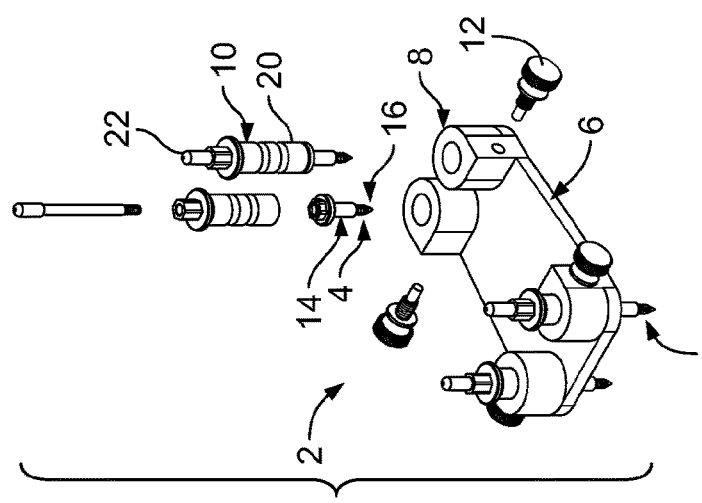
Figure 6:
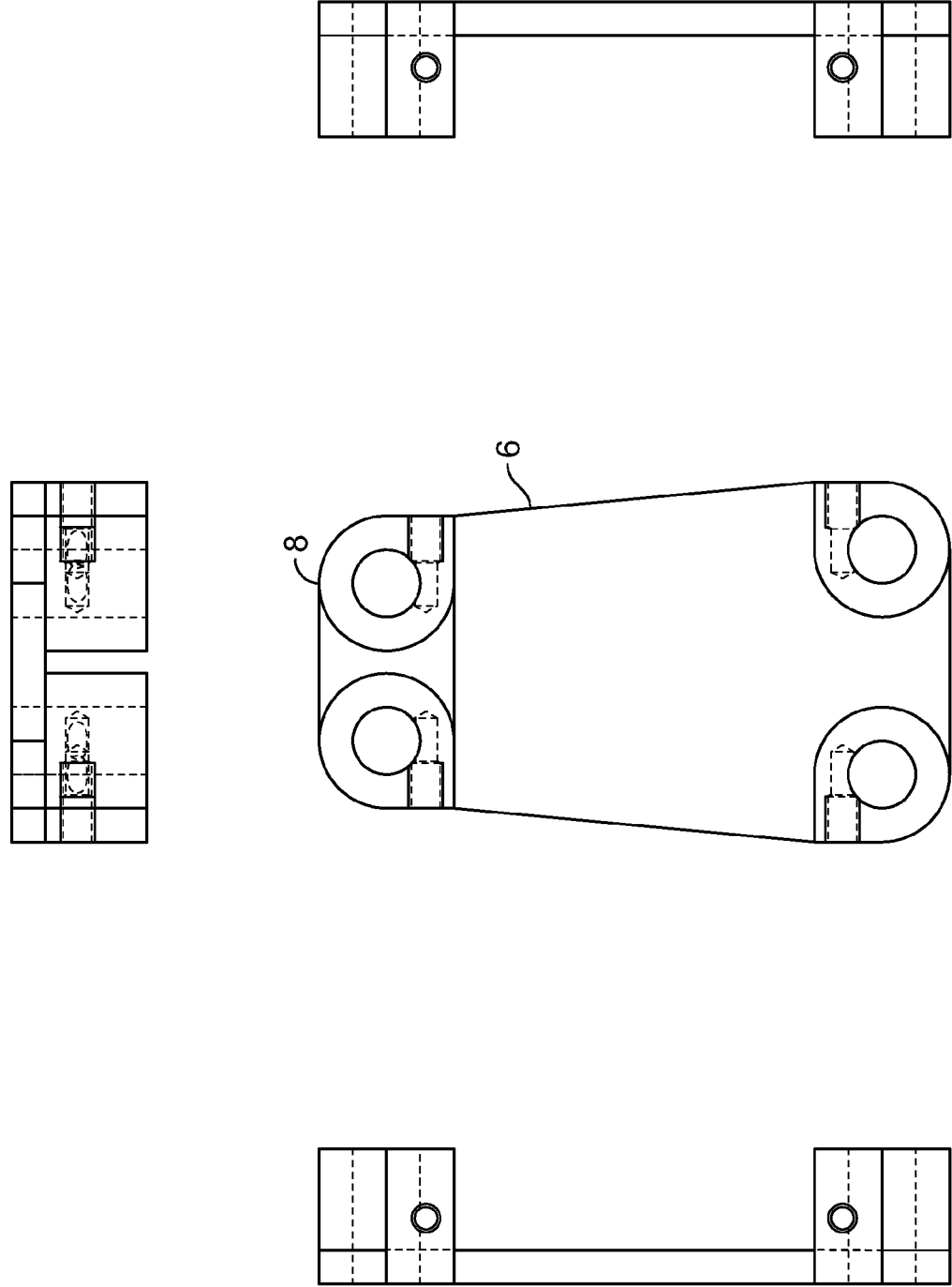
FIG. 6 illustrates various views of a platform of the template of FIGS. 1-5.
Figure 7:
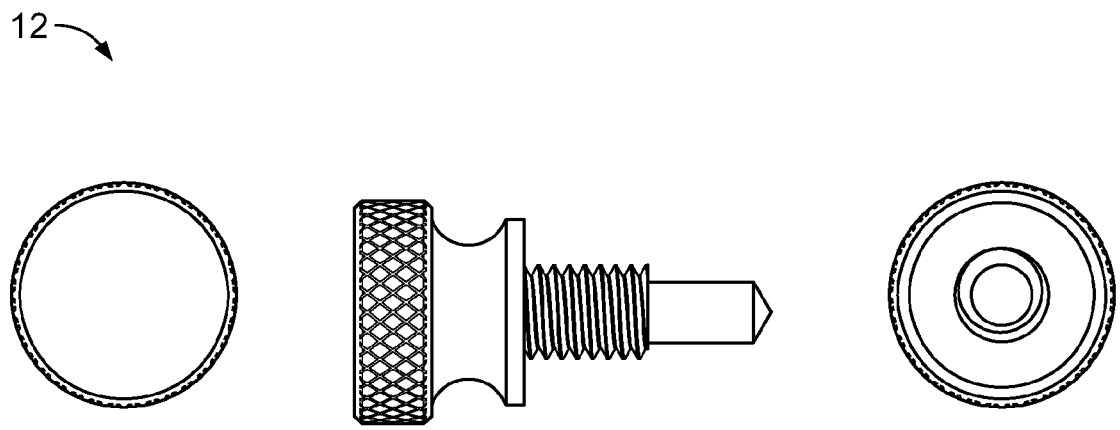
FIG. 7 illustrates various views of a locking screw of the template of FIGS. 1-5.

FIGS. 1-7 illustrate a screw template 2 and portions thereof that can be used to secure one or more anchor screws 4 to a mammalian skull. Various surgical devices (e.g., an image localizer frame for medical imaging modes, such as MRI, CT, PET, and DSA; a surgical platform; drill guides and a telemetry device) can be reversibly installed to the anchor screws 4 to carry out a neurosurgical procedure. Example neurosurgical procedures include deep brain stimulation (DBS), stereoelectroencephalography (SEEG), fiber optic ablation, intracranial biopsies, intraventricular shunts, extraventricular drains (EVD), third ventriculostomy, and tumor access (e.g., for biopsy/resection).

The template 2 includes a platform 6, four channels 8 that easily and quickly locate the anchor screws 4, and a driver assembly 10 by which the anchor screws 4 can be advanced into the skull. The channels 8 locate the anchor screws 4 in a defined arrangement (e.g., a precise geometric pattern) that determines positions of the anchor screws 4 with respect to each other. The arrangement corresponds to attachment points on the surgical devices that are used to carry out the neurosurgical procedure. For example, an interface between a surgical device and the anchor screws 4 may be provided as a plane defined by three or more anchor screws 4 or as an arc that enables a wide range of targets. The arrangement also allows for rotation of attached stereotactic devices in 90° increments, thereby reducing dead zones that may otherwise be caused by mechanical interference with skull anchoring features. Accordingly, the arrangement permits bilateral and posterior trajectories in the surgical plan. The screw template 2 also includes four locking screws 12 that respectively secure the driver assemblies 10 within the channels 8.

Figure 8:
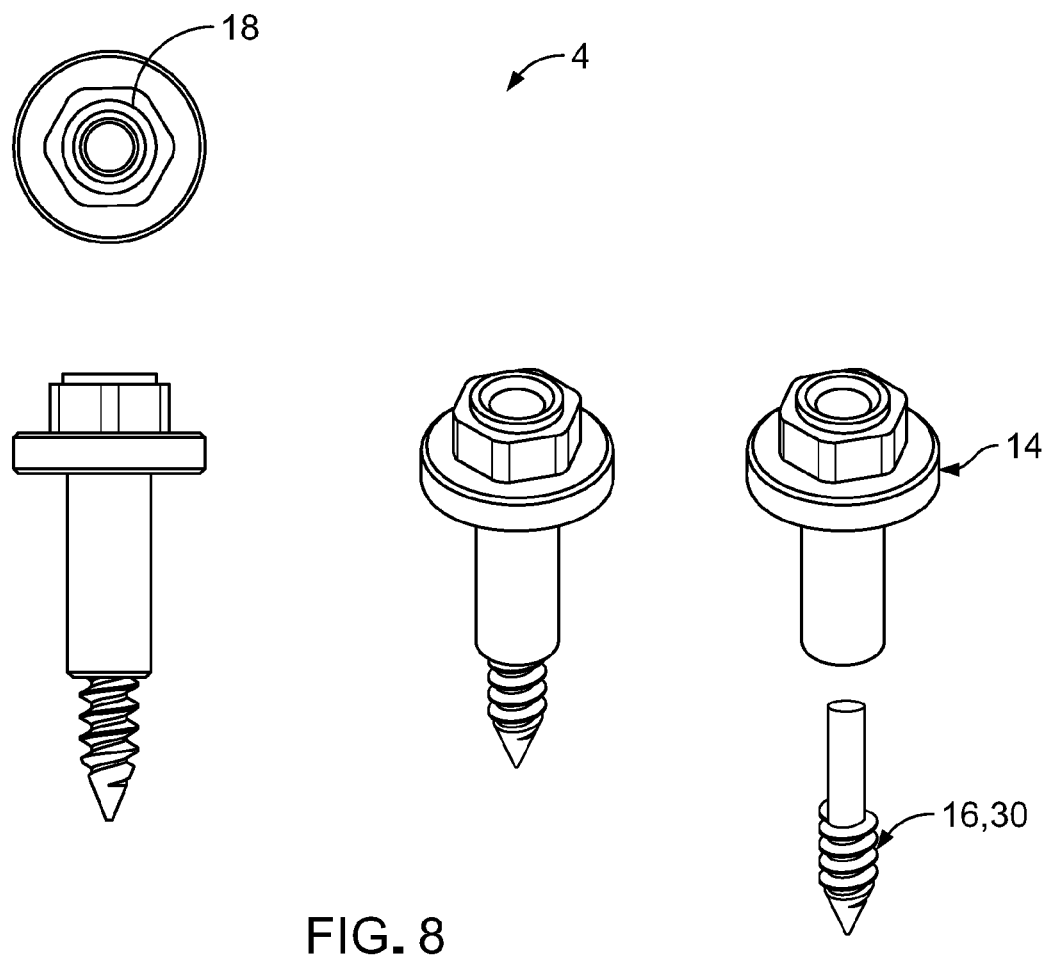
FIG. 8 illustrates various views of the anchor screws of FIGS. 1-5.
Figure 9:
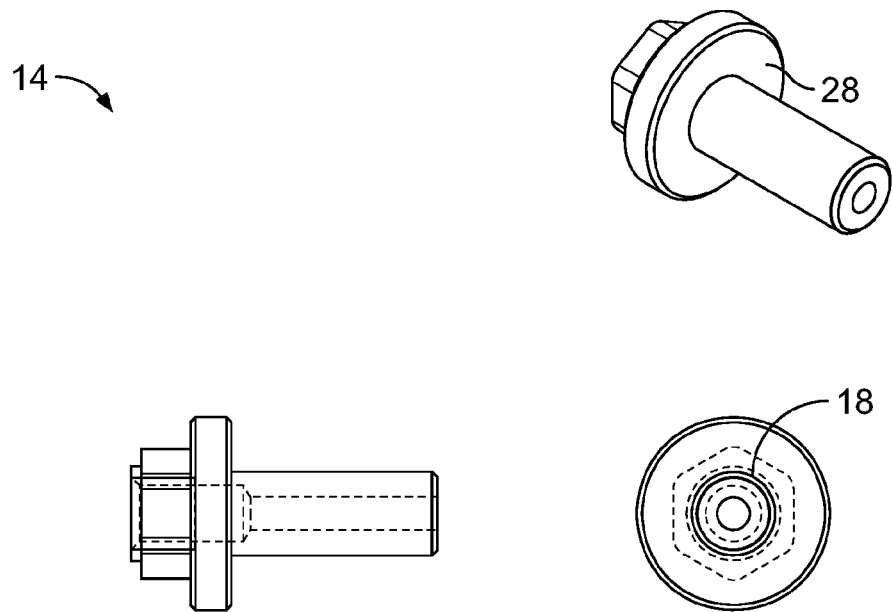
FIG. 9 illustrates various views of an anchor body of the anchor screws of FIG.
Figure 10:
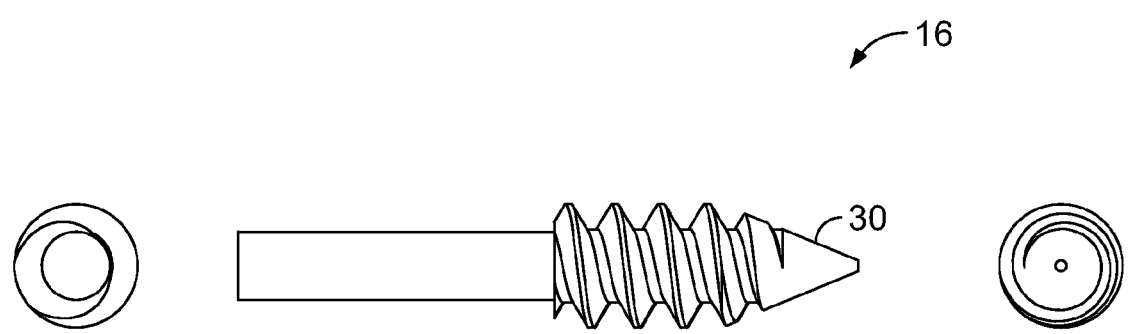
FIG. 10 illustrates various views of a screw tip of the anchor screws of FIG.

Referring to FIGS. 8-10, each anchor screw 4 includes an anchor body 14 that maintains engagement with the skull and a screw tip 16 that creates a passageway for the anchor body 14 in the skull. The screw tip 16 has a self-tapping thread 30. The thread 30 has threads per inch in a range of 12-20, with a fine pitch at a distal end to ease driving of the anchor screw 4. The screw tip 16 is welded to the anchor body 14. The anchor body 14 includes an internal thread 18 that interfaces with the driver assembly 10.

Figure 13:
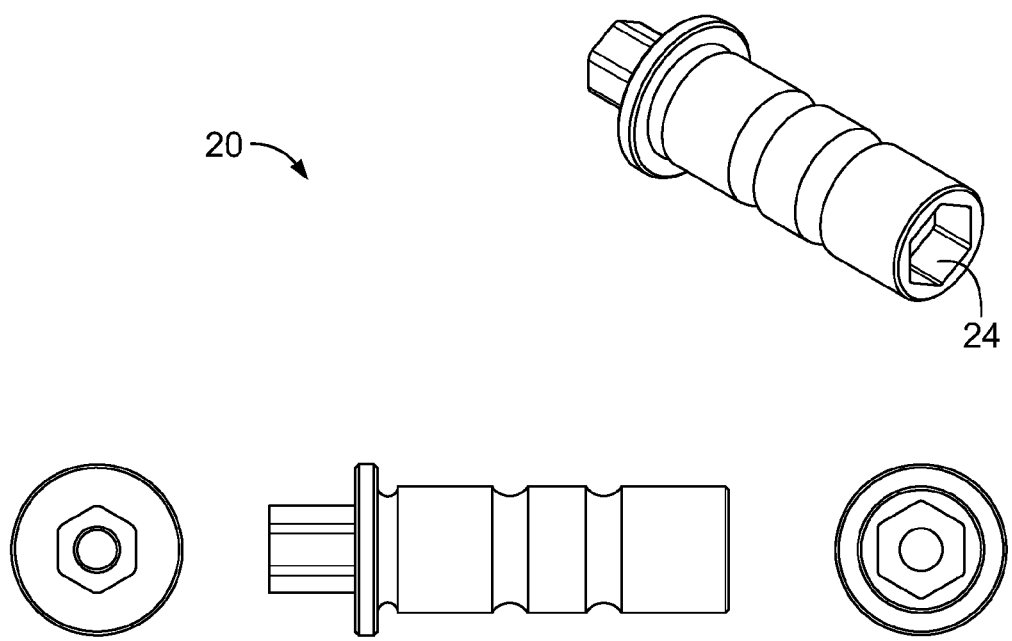
FIG. 13 illustrates various views of a screw driver of the driver assembly of FIG. 11.

Referring to FIGS. 11-13, each driver assembly 10 includes a screw driver 20 and a retaining rod 22. The screw driver 20 includes a pocket 24 that is formed to interface with the anchor body 14. The retaining rod 22 is sized to pass through the screw driver 20 and includes a threaded end 26 that screws into the internal thread 18 of the anchor body 14 to secure the screw driver 20 to the anchor screw 4. The retaining rod 22 includes a stop 27 that abuts the screw driver 20 and that, by threaded engagement with the anchor screw 4, can be used to drill the anchor screw 4 into the skull.

The anchor screws 4 are typically made of one or more materials that are compatible with 1.5T, 3.0T, and 7.0T MRI, such as titanium, ceramics, synthetic sapphire, polyoxymethylene (POM), PEEK, and other polymers. According to a material formulation and a structure of the anchor screws 4, the anchor screws 4 are strong enough to support the various surgical devices to be attached to the anchor screws during the neurosurgical procedure. The anchor screws 4 may be manufactured via one or more processes including 3D printing, injection molding, and machine operations, such as fabrication using computer numerical control (CNC) mills and lathes. The template 2 is typically made of one or more materials including aluminum, titanium, and stainless steel and is typically manufactured via one or more processes including CNC mills and lathes.

While example dimensions of the screw template 2 and the anchor screws 4 are shown in FIGS. 6, 7, 9, 10, and 12, one of ordinary skill in the art will understand that screw templates and anchor screws that are otherwise substantially similar in construction and function to the screw template 2 and the anchor screws 4 may have one or more dimensions that are different from those shown. In some embodiments, such dimensions may vary depending on a type of mammal to which the anchor screws 4 will be secured.

An initial stage of the neurosurgical procedure includes positioning the template 2, with the four anchor screws 4 locked in the channels 8, at a predetermined location atop the skull (e.g., at the outer table and diploe of the skull) following application of a local anesthetic. Each anchor screw 4 is sequentially implanted and secured into the skull until stops 28 of the anchor bodies 14 of the anchor screws 4 contact an external surface of the skull through a process of drilling a hole in the skull, tapping the hole, and tightening the anchor screw 4 into the hole. The locking screws 12 are then removed (e.g., unscrewed) from the channels 8, and the retaining rods 22 are removed (e.g., unscrewed) from the anchor screws 4. The screw drivers 20, sitting atop the anchor screws 4, are removed (e.g., pulled upward) from the anchor bodies 14 of the anchor screws 4, while the screw tips 16 remain at subcutaneous locations within the skull. In some implementations, the anchor screws 4 can be used with pilot holes. Once the anchor screws 4 are secured to the skull, multiple devices can be attached to the anchor screws 4 to carry out different surgical procedures.

Figures 14, 15:
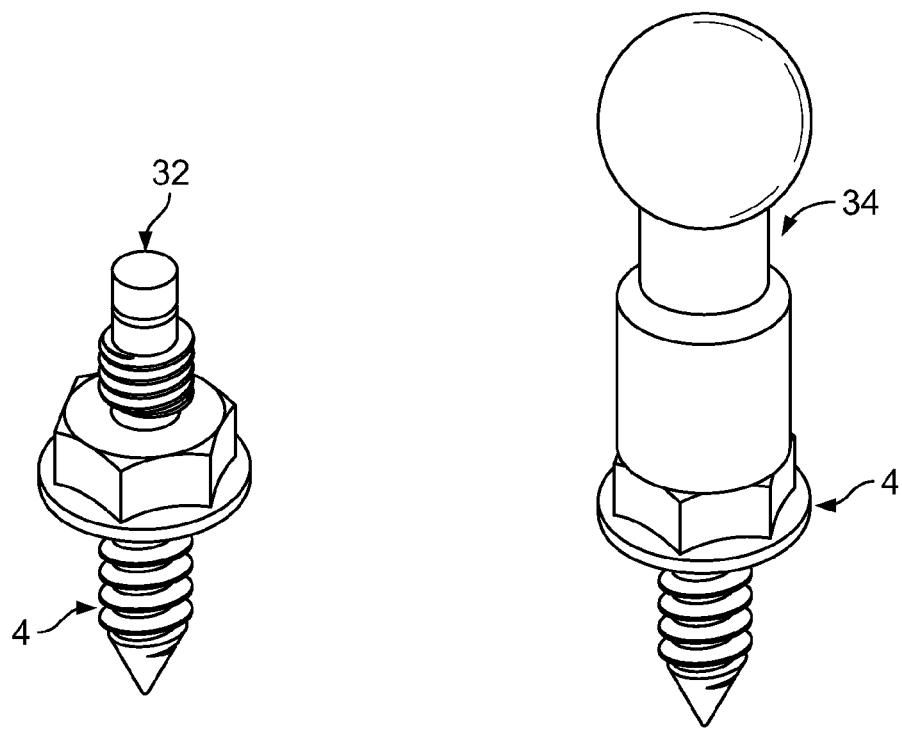
FIG. 14 illustrates an anchor screw of FIGS. 1-5 with a screw joint.
FIG. 15 illustrates an anchor screw of FIGS. 1-5 with a standoff.

In some embodiments, standoffs can be secured to the anchor screws 4 after removal of the template 2 in order to position a surgical device at a desired spacing from the skull. For example, FIG. 14 illustrates a threaded screw joint 32 that is threaded within the internal thread 18 of the anchor screw 4, and FIG. 15 illustrates a standoff 34 including an internal thread that secures the standoff 34 to the threaded screw joint 32.

Figure 16:
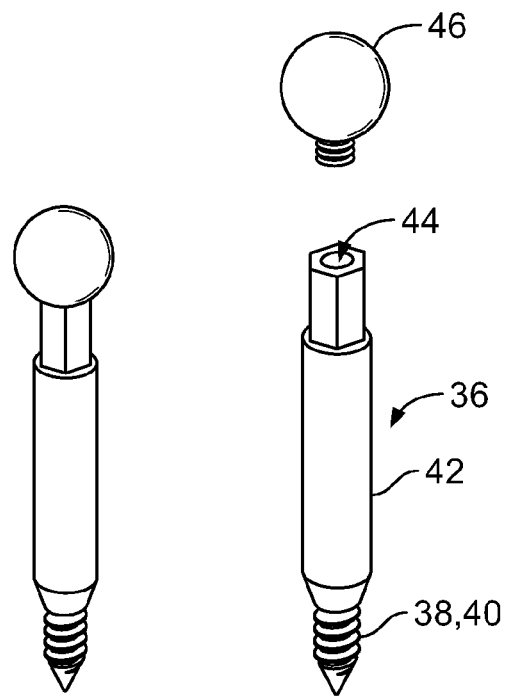
FIG. 16 illustrates an anchor screw including a standoff.

FIG. 16 illustrates an anchor screw 36 that can be used with the template 2 to perform a neurosurgical procedure. The anchor screw 36 includes a screw tip 38 with a self-tapping thread 40, an anchor body 42 that includes an internal thread 44, and a standoff 46 that can be threaded into the internal thread 44 of the anchor body 42. The anchor body 42 protrudes from the skull during surgery. The standoff 46 is a detachable ball structure that can interface with (e.g., provide attachment sites for) appropriate receiving components of surgical devices to be attached to the anchor screws 36.

In some embodiments, the anchor body 42 has a height of about 0.5 cm to about 0.8 cm (e.g., about 0.7 cm), and the standoff 46 has a diameter (e.g., a width) of about 0.5 cm to about 0.7 cm (e.g., about 0.6 cm). The anchor body 42 and the screw tip 38 are made of the same one or more materials as described above for the anchor screws 4. Standoff 46 are typically made of ceramic (e.g., for use during imaging) or stainless steel (e.g., for use during the neurosurgical procedure). While the standoff 46 is illustrated as a ball top design, in some embodiments, anchor screws that are otherwise substantially similar in construction and function to the anchor screw 36 includes detachable standoffs that have a cylindrical shape. Such standoffs can interface with (e.g., provide attachment sites for) appropriate receiving components of surgical devices to be attached to the anchor screws.

Figure 17:
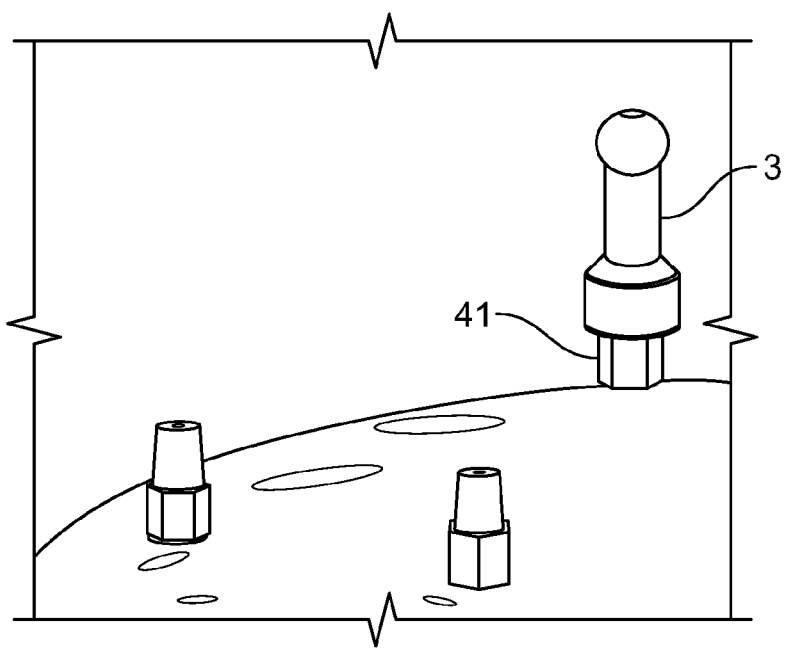
FIG. 17 illustrates an anchor screw with a standoff.

FIG. 17 illustrates another embodiment of ball-type standoffs 3 that can be installed to anchor screws 41.

Figure 18:
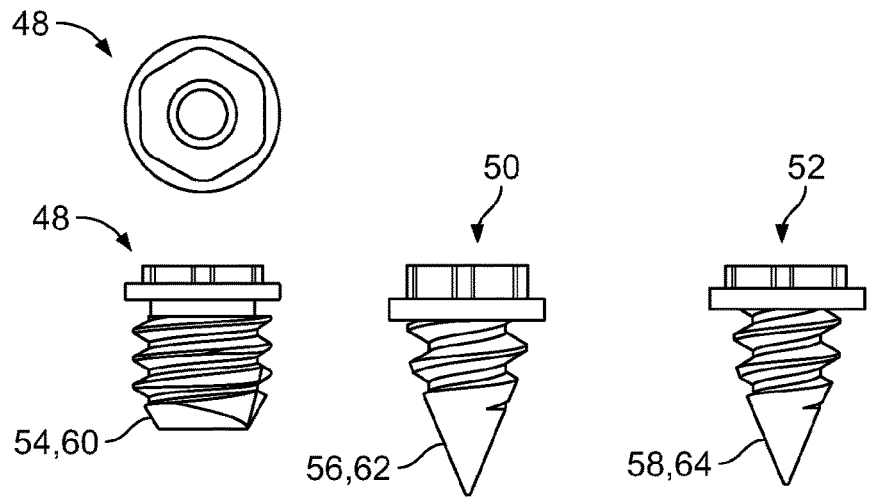
FIG. 18 illustrates multiple views of various embodiments of subcutaneous screw tips.
Figure 19:
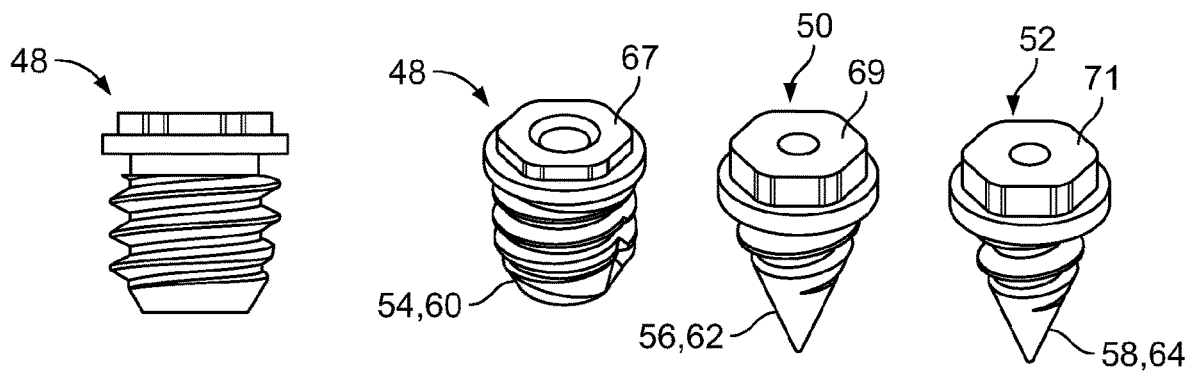
FIG. 19 illustrates multiple views of the subcutaneous screw tips of FIG. 18.

Anchor screws as discussed herein can include screw tips of various designs. For example, FIGS. 18 and 19 illustrate side and perspective views of anchor screws 48, 50, 52 that have different screw tips 54, 56, 58 with different types of self-tapping threads 60, 62, 64. Additional views of anchor screw 48 are also illustrated. Anchor bodies 67, 69, 71 of the anchor screws 48, 50, 52 include internal threads for connection to standoffs.

Figure 20:
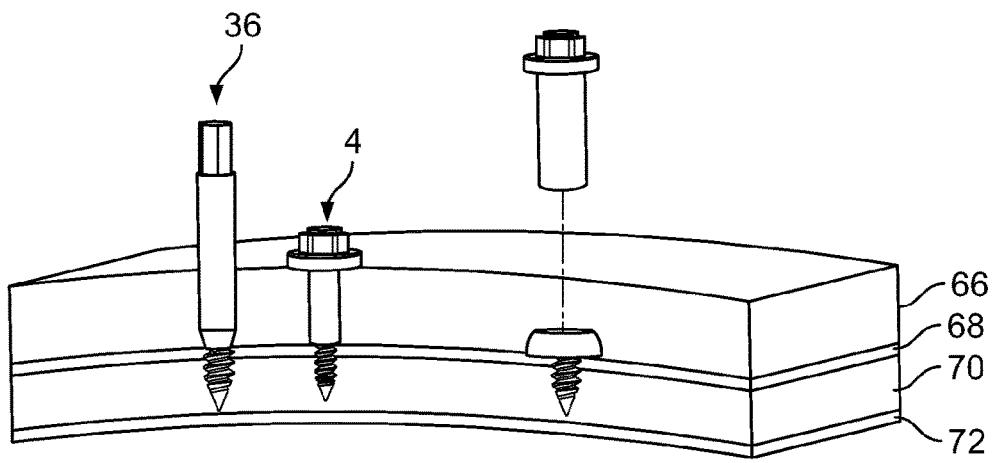
FIG. 20 illustrates various anchor screws attached to a skull.

FIG. 20 illustrates example implantations of an anchor screw 4, an anchor screw 36 (standoff 46 omitted), and an anchor screw 52 within a skull. The anchor bodies protrude from the scalp (red layer) 66, and the screw tips extend within the outer table of the skull 68 (blue layer) and diploe 70 (green layer), but do not reach the inner table of the skull 72 (pink layer).

The anchor screws 4, 36, 48, 50, 52 can provide reference marks during an initial stage of the neurosurgery in which MM takes place. For example, the anchor screws 4, 36, 48, 50, 52 can allow registration of image space and stereotactic space. Accordingly, any portion of the anchor screws 4, 36, 48, 50, 52 (e.g., the screw tips, the anchor bodies, or the standoffs) may include line of site or non-line of site approaches for tracking. In some embodiments, the anchor screws 4, 36, 48, 50, 52 include one or more of an active element with a radio frequency (RF) emitter, an infrared LED, a reflective infrared sphere, or an aqueous or non-aqueous metallic or non-metallic chemical that is visible in MRI. For example, the standoffs may contain a cavity filled with a substance (e.g., $CuSO_4$ water solution, vitamin E oil, mineral oil, petroleum jelly, etc.) that provides an image reference mark at a known location in stereotactic space. Profiles of the reference marks can be scanned and used for surface matching to the various surgical devices during the neurosurgical procedure. In some instances, a 3D scanning camera can be used to generate a physical profile of the patient and of the standoffs.

Figure 21:
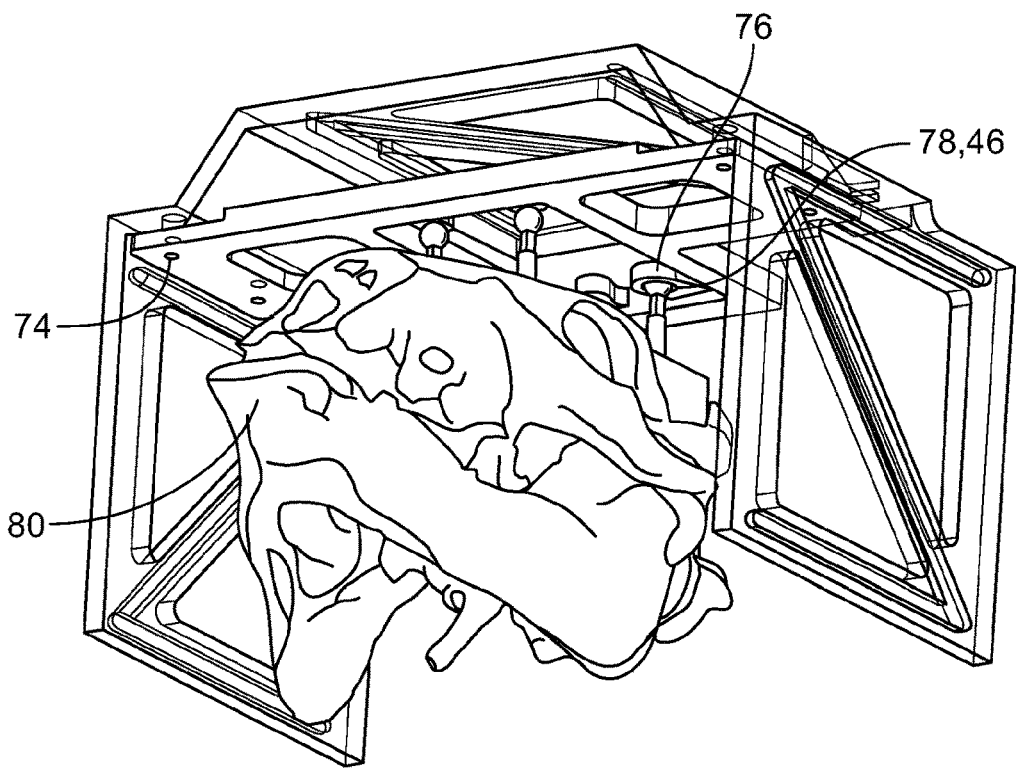
FIGS. 21 and 22 illustrate various views of an imaging frame engaged with the anchor screws of FIG. 17.
Figure 22:
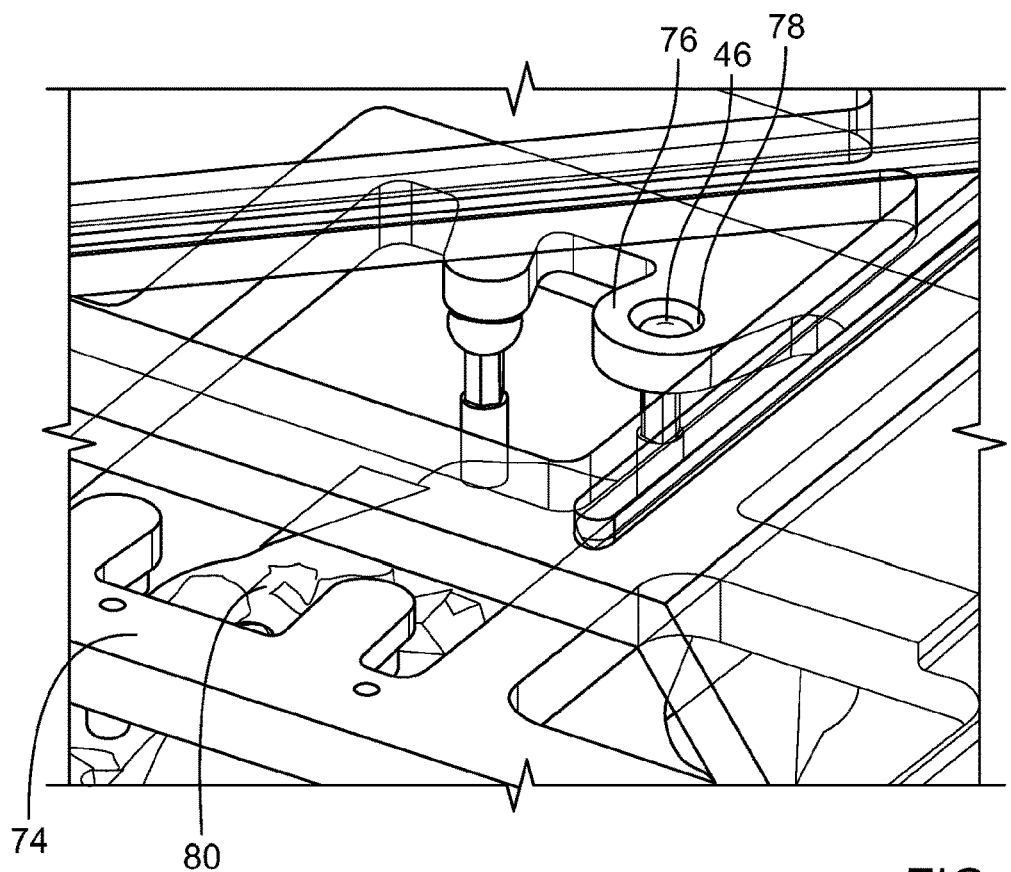
Figure 23:
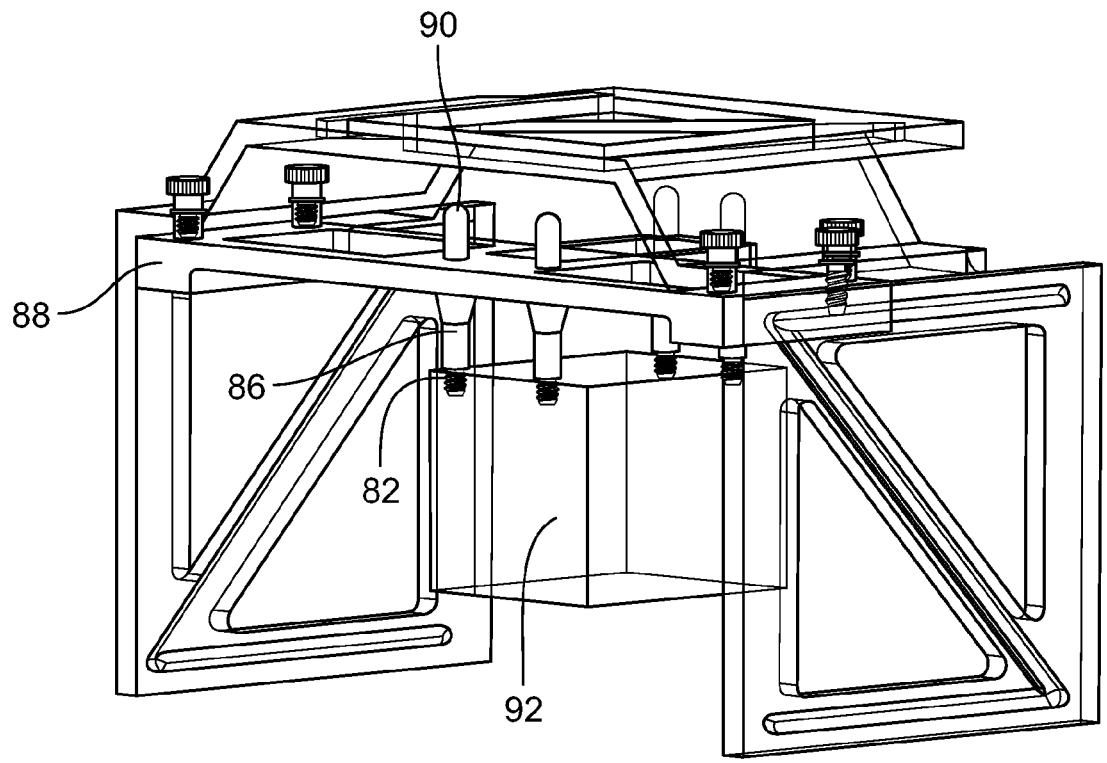
FIG. 23 illustrates an imaging frame engaged with standoffs attached to anchor screws.

A first phase of a neurosurgical procedure includes an imaging and planning protocol. FIGS. 21 and 22 illustrate an interface between the anchor screws 36 (anchored in a skull 80) and an imaging frame 74 (e.g., an image localizer). The imaging frame 74 includes four arms 76 with circular pockets 78 that engage the standoffs 46. In another embodiment, FIG. 23 illustrates an interface between anchor screws 82 (anchored in a skull 92) and an imaging frame 88 (e.g., an image localizer). The anchor screws 82 include post-style standoffs 86. The imaging frame 88 is secured to the standoffs 86 with corresponding caps 90. Once the imaging and planning protocol is completed, the imaging frame is removed from the standoffs, the standoffs are removed from the anchor screws, and the anchor screws (e.g., excluding the standoffs) remain secured to the skull 80 so that a stereotactic device can be attached to the anchor screws in a second stage of the neurosurgical procedure. In this manner, an attachment of the anchor screws to the skull decouples the first stage from the second stage of the neurosurgical procedure, allowing a patient to leave a medical facility following completion of the first stage and to return to the medical facility for commencement of the second stage of the neurosurgical procedure.

Figure 24:
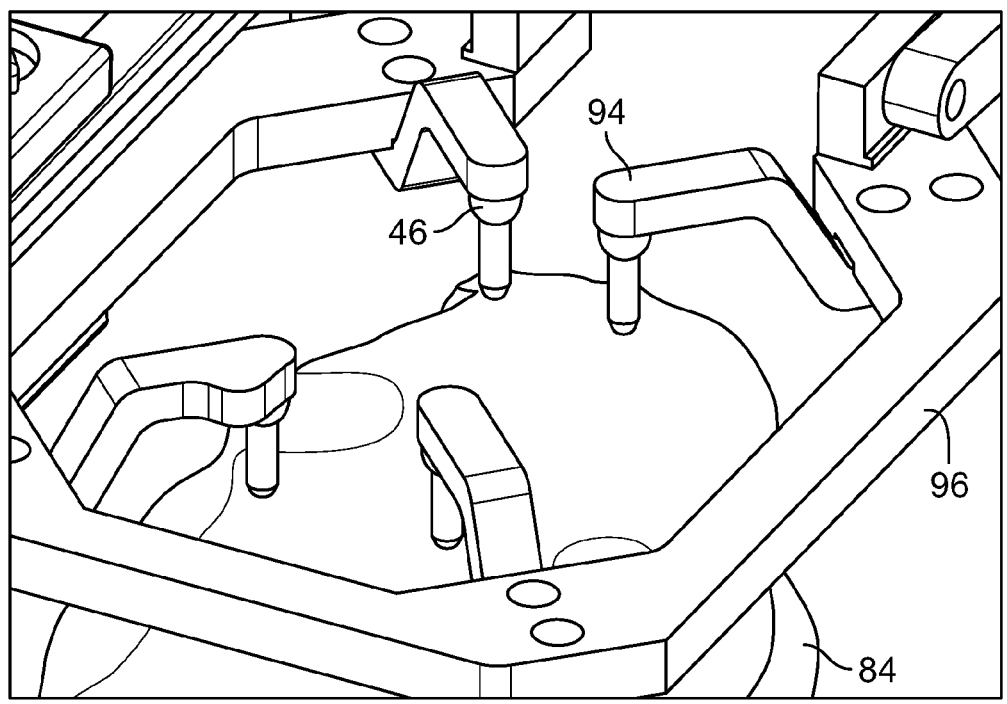
FIG. 24 illustrates a platform of a stereotactic device engaged with the anchor screws of FIG. 17.
Figure 25:
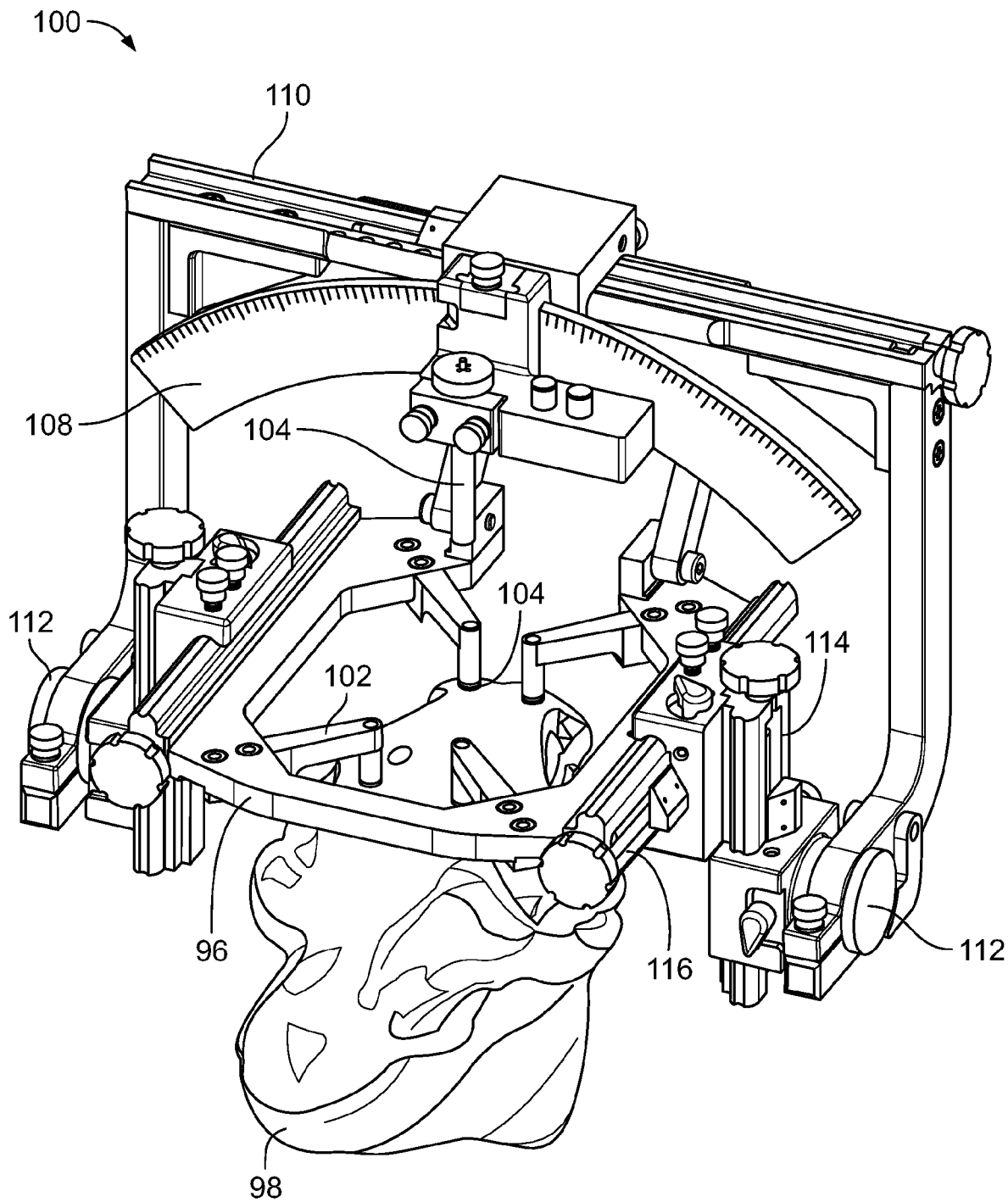
FIG. 25 illustrates a stereotactic device engaged with the anchor screws of FIGS. 1-5.
Figure 26:
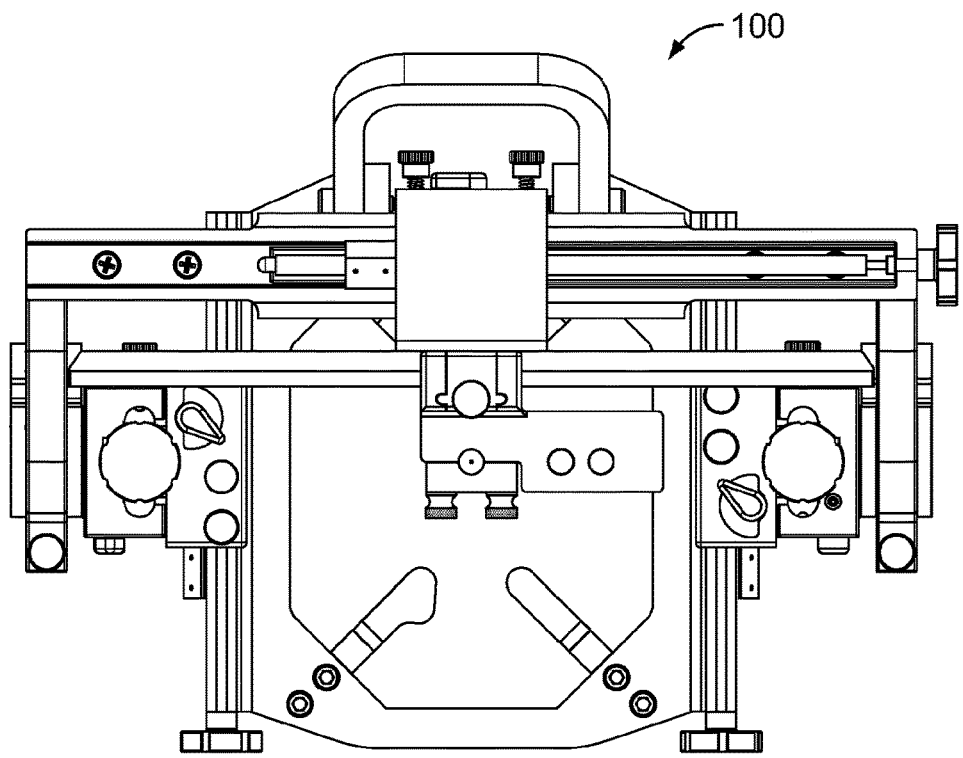
FIGS. 26-29 illustrate various views of the stereotactic device of FIG. 25.
Figure 27:
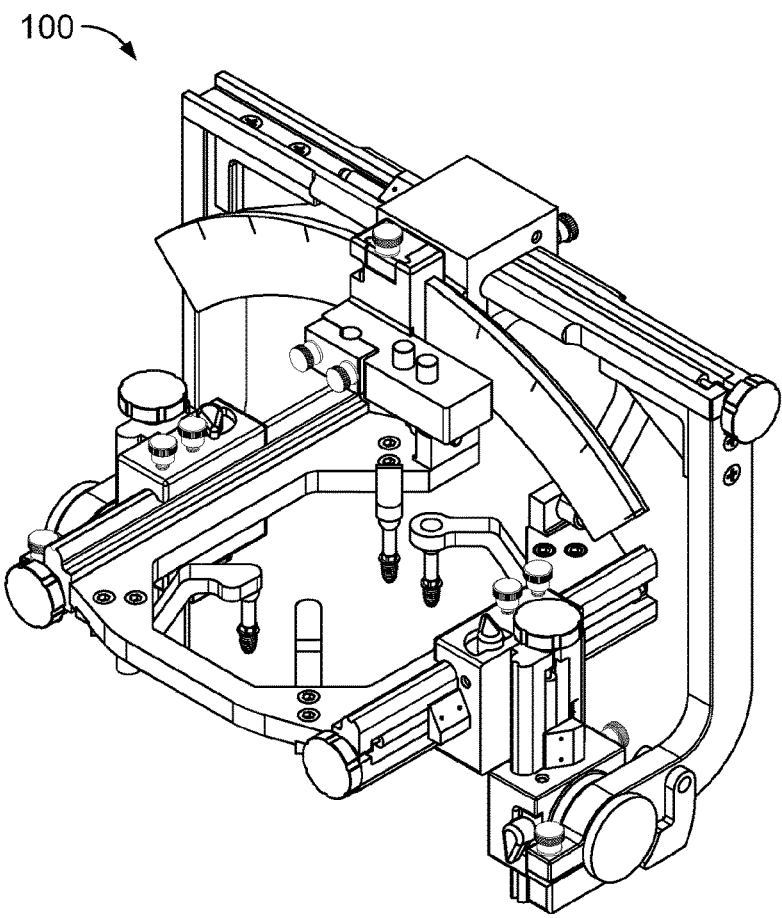
Figure 28:
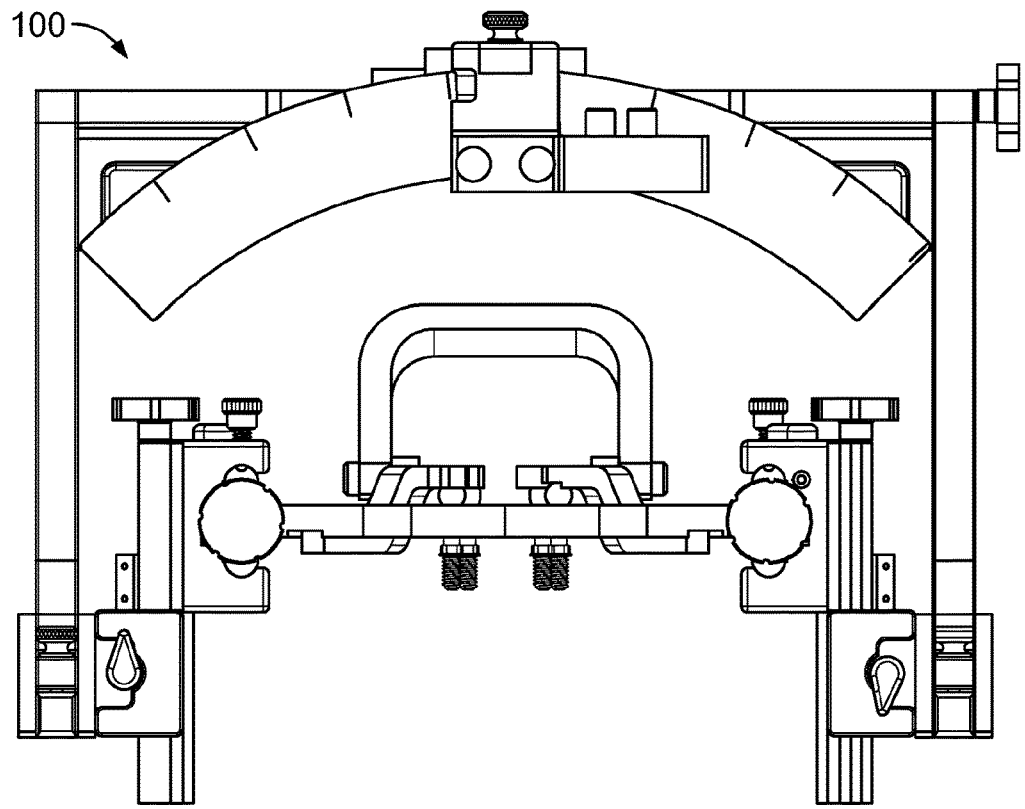
Figure 29:
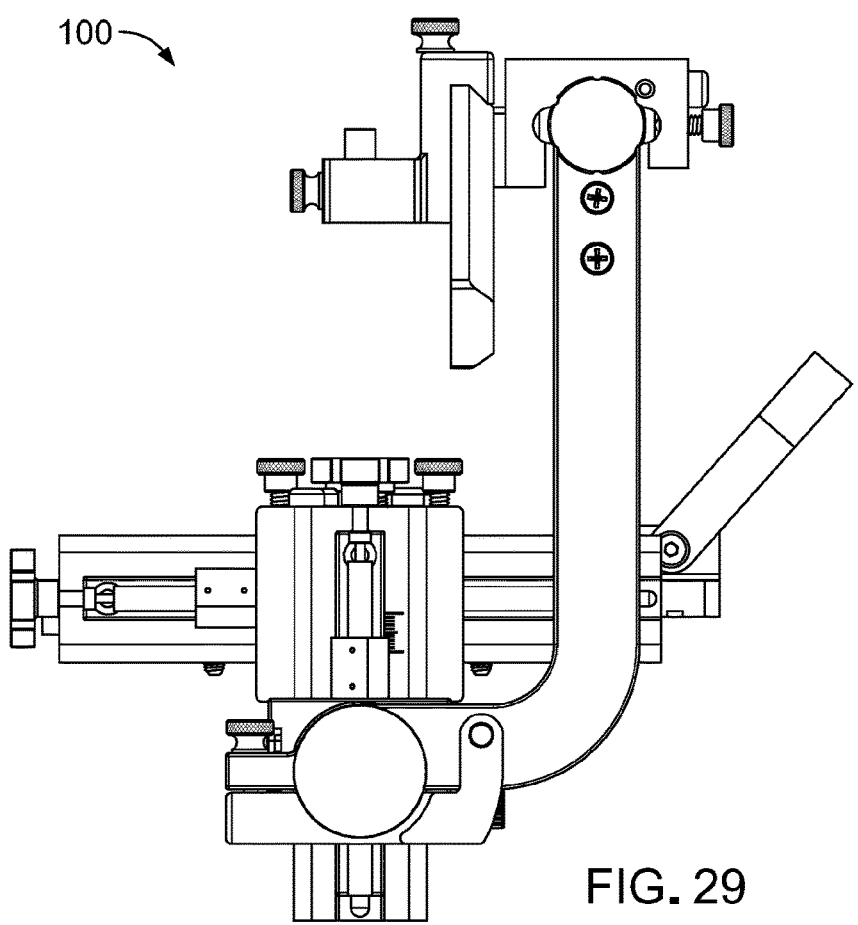
Figure 30:
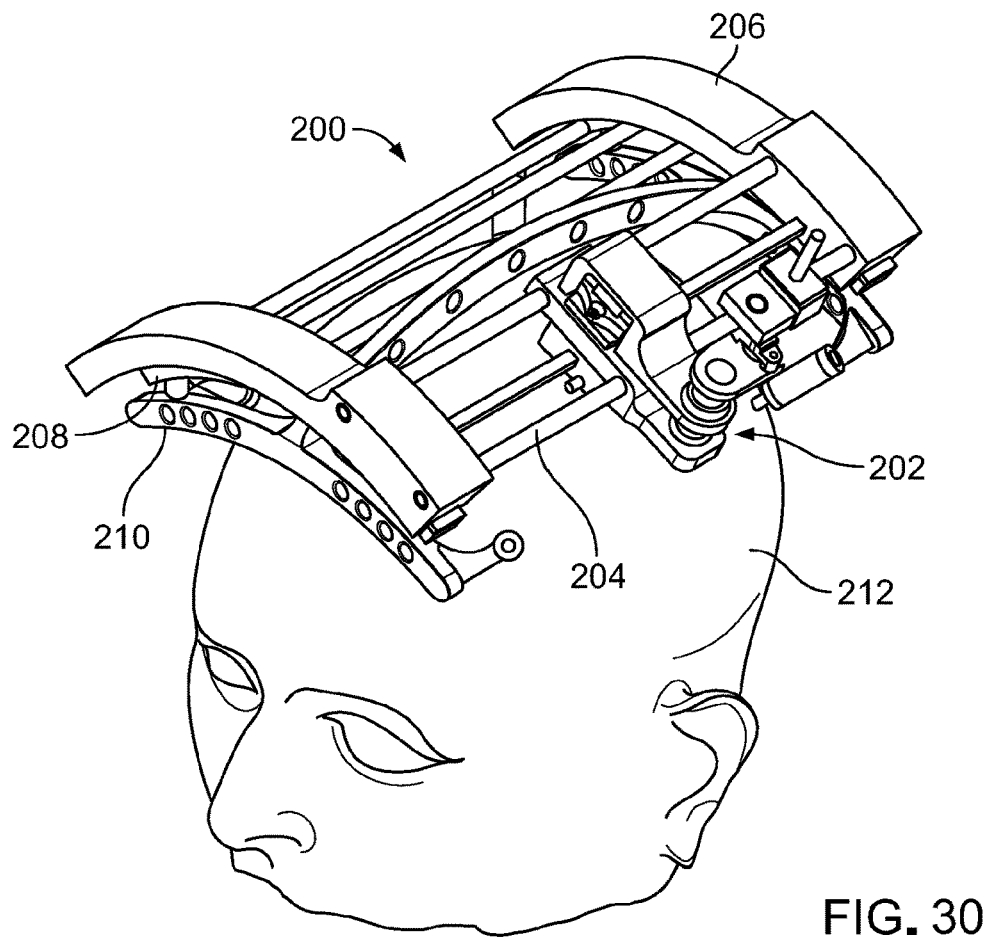
FIG. 30 illustrates a stereotactic device engaged with anchor screws that are secured to a patient skull.
Figure 31:
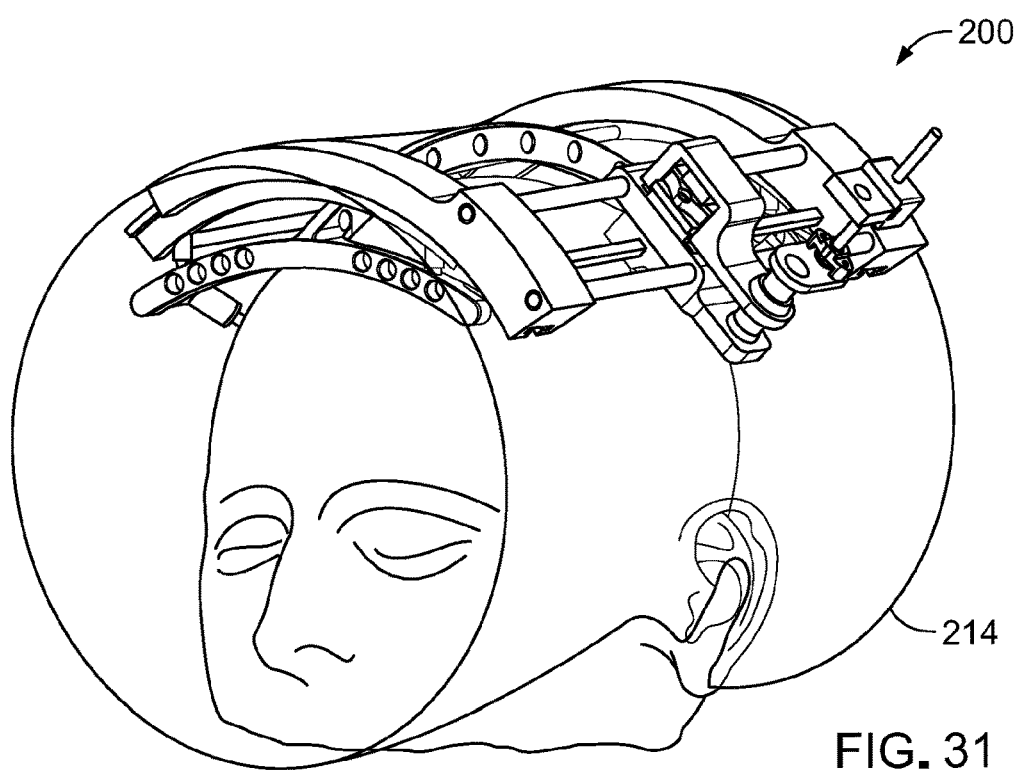
FIG. 31 illustrates a work envelope defined by the stereotactic device of FIG. 30.
Figure 32:
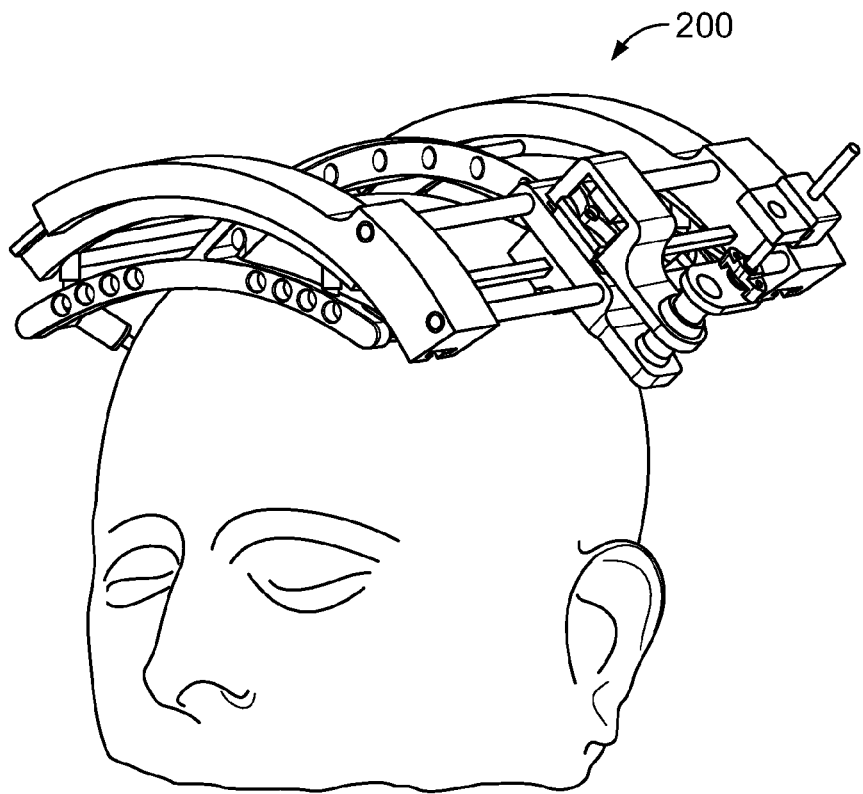
FIG. 32 illustrates various degrees of freedom provided by the stereotactic device of FIG. 30.

The second stage of the neurosurgical procedure includes execution of a surgical plan generated during the first stage of the neurosurgical procedure. FIG. 24 illustrates an interface between the anchor screws 36 (anchored in a skull 84) and a stereotactic device 100. (In some cases, the stereotactic device 100 may also be referred to as a stereotaxic device.) Four arms 94 are attached to a platform 96 of the stereotactic device 100. The arms 94 define circular pockets on an underside that engage the standoffs 46, thereby attaching the stereotactic device 100 to the skull 84 in FIG. 24 or to the skull 92 (illustrated schematically as a box) in FIG. 23. In another embodiment, FIG. 25 illustrates a direct interface between the anchor screws 4 (anchored in a skull 98) and the stereotactic device 100. Four arms 102 are attached to the platform 96 of the stereotactic device 100, and the arms 102 are attached to the anchor bodies 42 of the anchor screws 4, thereby attaching the stereotactic device 100 to the skull 98.

Referring to FIGS. 25-29, the stereotactic device 100 provides multiple degrees of freedom by which a guide 104 (e.g., an instrument carrier) of the stereotactic device 100 can be manually positioned for inserting electrode leads into the brain according to the surgical plan. The guide 104 is connected to and movable in a first degree of freedom (e.g., an arc angle) along an arc 108 (e.g., a ruled arc). The arc 108 is connected to and movable in a second degree of freedom (e.g., linear translation) along an upper horizontal rail 110. The upper horizontal rail 110 is connected to and movable in a third degree of freedom (e.g., a color angle) about two opposite pivot joints 112. The pivot joints 112 are connected to and movable in a fourth degree of freedom (e.g., linear translation) along vertical side rails 114. The vertical side rails 114 are connected to and movable in a fifth degree of freedom (e.g., linear translation) along respective, opposite horizontal end rails 116. The horizontal end rails 116 are attached to opposite sides of the platform 96 (e.g., fixed to the skull 92), such that ultimately, the guide 104 is positioned with respect to the skull 92 for appropriate insertion of electrode leads. The stereotactic device 100 further includes multiple locking screws, clamps, and other fastening mechanisms that fix the movable components in desired positions.

Various arm constructions (e.g., the arms 94, 102, or other arm constructions) can be attached to the platform 96, depending on the construction of anchor screws (e.g., and in some cases, attached standoffs) that are attached to the skull for connection to the stereotactic device 100. The stereotactic device 100 is small enough to fit within 1.5T. 3.0T, and 7.0T MRI apparatuses, as well as computed tomography (CT) apparatuses. In some embodiments, the stereotactic device 100 has a total length of about 20 cm to about 22 cm, a total width of about 30 cm to about 32 cm, and a total height of about 23 cm to about 25 cm. The various components of the stereotactic system 100 are typically made of one or more materials, including aluminum, ceramic, titanium, stainless steel, polyoxymethylene (POM), and PEEK. The various components may be manufactured via one or more processes including CNC milling and lathes, injection molding, and 3D printing.

In some implementations, and during the first stage of the neurosurgical procedure, a surgical planning software system generates a surgical plan that can be used with an automated stereotactic device. Referring to FIGS. 30-33, the stereotactic device 200 provides multiple degrees of freedom by which a guide 202 (e.g., an instrument carrier) of the stereotactic device 200 can be automatically positioned via image-guided robotics along a cylindrical work envelop 214 (see FIG. 31) for inserting electrode leads into the brain according to the surgical plan. The guide 202 is connected to and movable in a first degree of freedom Z (e.g., linear translation) along rails 204. The rails 204 are connected to an upper arc structure 206, which is connected to and movable in a second degree of freedom θ (e.g., angular movement) along a lower arc structure 208. A radius R of the arc structures 206, 208 (e.g., and accordingly, a radius of the cylindrical work envelope illustrated in FIG. 31) is fixed by a construction of the stereotactic device 200 and defines a third position coordinate of the guide 202. The first and second degrees of freedom and the third position coordinate together locate an entry point, as defined by the surgical plan.

Figure 33:
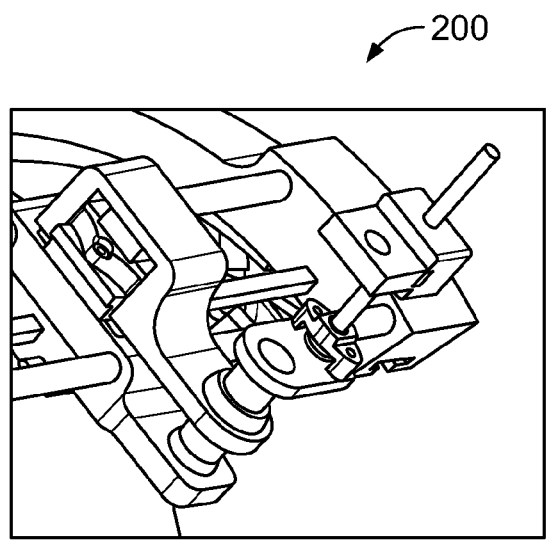
FIG. 33 illustrates various degrees of freedom provided by the stereotactic device of FIG. 30.

The guide 202 has three more degrees of freedom that sets the electrode lead onto the surgical trajectory, such that the stereotactic device 200 has five degrees of freedom. These degrees of freedom include a roll, a pitch, and a depth, as shown in FIG. 33. A combination of the pitch and the roll adjusts a tilt of the guide 202 and are determined by the surgical planning software system. The lower arc structure 208 is attached to opposite sides of a platform 210 (e.g., fixed to the skull 212 at anchor screws 204), such that ultimately, the guide 202 is positioned with respect to the skull 212 for appropriate insertion of electrode leads. A trajectory along which the electrode lead is delivered depends on an angle of the gimbal. The actuation control is performed using piezo electric linear motors mounted perpendicular to each other. This is a unique design that converts the linear motion of the motors to the pitch and roll rotations of the double gimballed device.

The guides 102, 202 of the stereotactic devices 100, 200 allow for low-profile fixation within a burr hole and automatic captivation of depth electrode lead upon removal of a lead delivery cannula. Additionally, the guides 102, 202 are designed to both house and protect electrode leads prior to connection to a pulse generator or another device.

FIGS. 34-40 illustrate a skull attachment device 300 that can be used to secure various stereotactic surgical devices to a skull to carry out a neurosurgical procedure. The skull attachment device 300 is compatible with 7.0T MRI and can secure all components of a cooperating stereotactic system to the patient's skull. For example, the stereotactic system may include a stereotactic positioning device, a CT image localizer, an MRI localizer, and other stereotactic devices. The skull attachment device 300 remains attached to the skull for the duration of the stereotactic process such that the spatial orientation of image space and stereotactic space are aligned for as long as a location of skull attachment device 300 remains unaltered. This capability allows acquisition of a planning MRI exam and surgical planning to occur on one day, while the surgery is performed on a subsequent day (e.g., the next day). Advantageously, this allows the planning MRI exam and the surgical planning to occur outside of the OR such that the OR only needs to be utilized the surgical procedure. This approach greatly improves the efficiency of OR time and reduces the overhead associated with performing a stereotactic procedure. In some examples, a surgeon may perform the surgical sequence in a single day if that is desired.

The skull attachment device 300 includes a base 302, a forward protrusion 304, two opposing lateral protrusions 306, three sharp titanium pins 308, and an interface 310 that extends upward from a top surface 312 of the base 302. The base 302 defines four holes 314 by which a cooperating stereotactic device can be attached to the skull attachment device 300 via screws, pins, or the like. The pins 308 extend downward from the forward protrusion 304 and from a rear portion of the base 302. The pins 308 are designed to penetrate a patient's scalp and seat into an outer table of a skull 301. Each lateral protrusion 306 defines a hole 316 through which a titanium skull anchor screw 318 can be passed to securely attach the skull attachment device 300 to the skull 301, as illustrated in FIG. 39. Opposing forces applied by the screws 318 and by the pins 308 immobilize the skull attachment device 300 on the skull 301.

The skull attachment device 300 defines an angle a between the top surface 312 and a lower surface 320 of the base 302. The skull attachment device 300 may be designed such that the angle α is selected from a range of values to accommodate variable topography of human skulls to ensure that an orientation of the stereotactic device is orthogonal to a long axis of the human body. For example, the top surface 312 is oriented horizontally, while the lower surface 320 can vary in angular orientation. In some embodiments, the angle α is in a range of about 0 degrees (as shown in FIG. 39) to about 40 degrees (as shown in FIGS. 34-38 and 40-48). In some embodiments, the angle α may be selectable from the range in 10 degree increments (e.g., about 0, 10, 20, 30, or 40 degrees).

Figure 40:
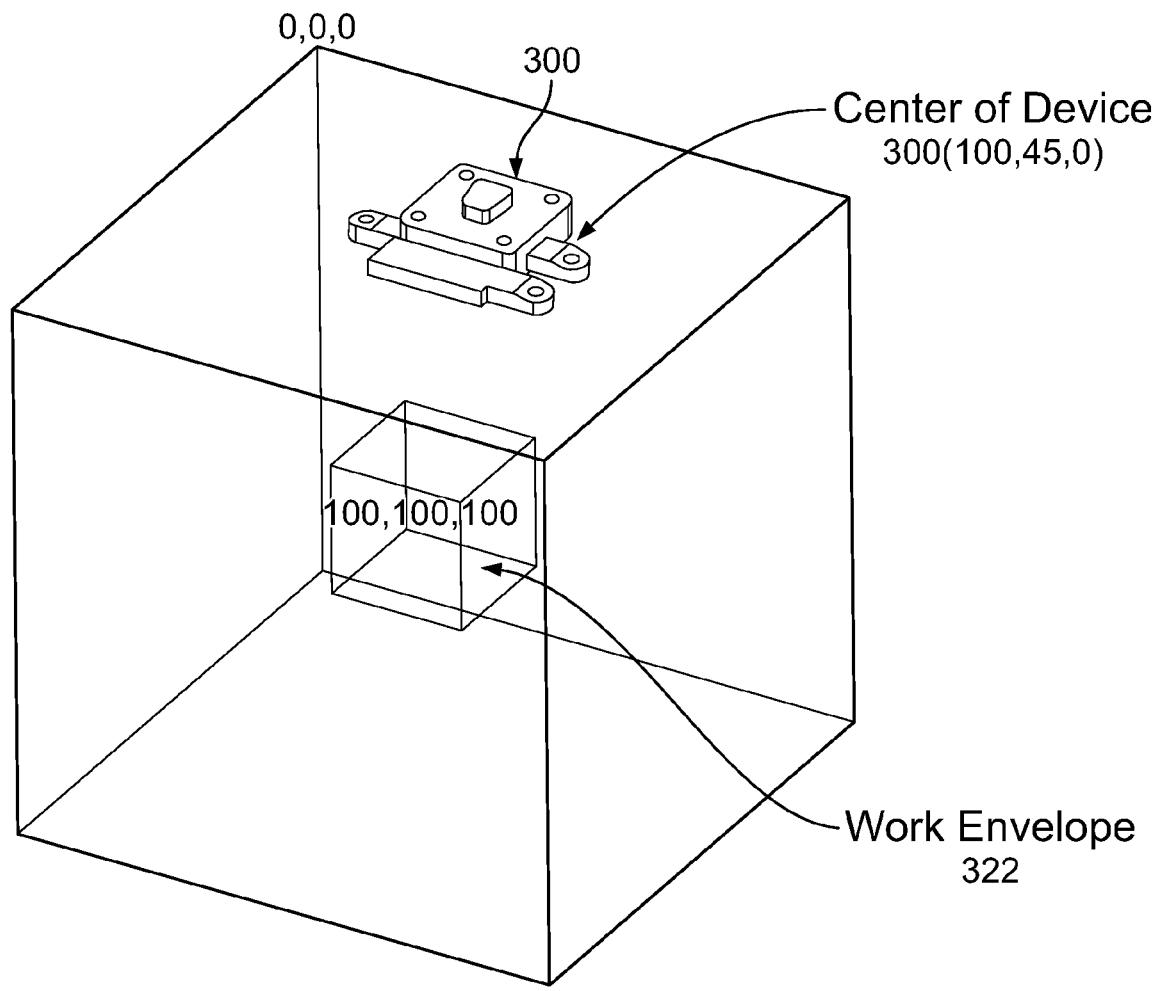
FIG. 40 illustrates a stereotactic coordinate system defined by the skull attachment device of FIGS. 34-38.

The interface 310 serves as an indexing profile (e.g., a keyed surface) that determines and maintains an orientation and a position of a cooperating stereotactic device with respect to the skull attachment device 300 to which the stereotactic device is attached via the holes 314. That is, the skull attachment device 300 maintains a constant spatial relationship between the stereotactic device and the patient's skull 301. Accordingly, while the interface 310 has lateral symmetry, the interface 310 is radially asymmetric. Referring particularly to FIG. 40, the top surface 312 of the skull attachment device 300 defines a reference plane that establishes a spatial orientation of an XYZ stereotactic coordinate system in which a work envelope 322 is positioned. For example, the reference plane (e.g., the top surface 312) is located at a vertical position of Z=0, and a center point of the reference plane has a horizontal position of X=100 and Y=45.

In some embodiments, the skull attachment device 300 may be manufactured via 3D printing and may be made of a thermoplastic material, such as POM, to render the skull attachment device 300 compatible with an MRI system. In other embodiments, the skull attachment device 300 may be made of aluminum or titanium. The base 302 of the skull attachment device 300 typically has a length of about 45 mm to about 48 mm, a width of about 45 mm to about 48 mm, and a minimum thickness of about 12 mm to about 45 mm. The skull attachment device 300 typically weighs about 13 g to about 70 g.

Attaching the skull attachment device 300 to the skull 301 begins with anesthetizing the scalp at each site of the pins 308 and the screws 318. The two posterior pins 308 are seated first onto the skull 301, followed by the anterior pin 308. The screws 318 are inserted through the holes 316 and screwed into the skull 301. Equal torque is applied to each screw 318. The procedure of applying the skull attachment device 300 to the patient's skull 301 is simple and safe enough to be performed outside of an operating room (OR). For example, an exam room or a patient room suffices for performing this procedure, such that OR time is not required to perform this procedure.

Figure 41:
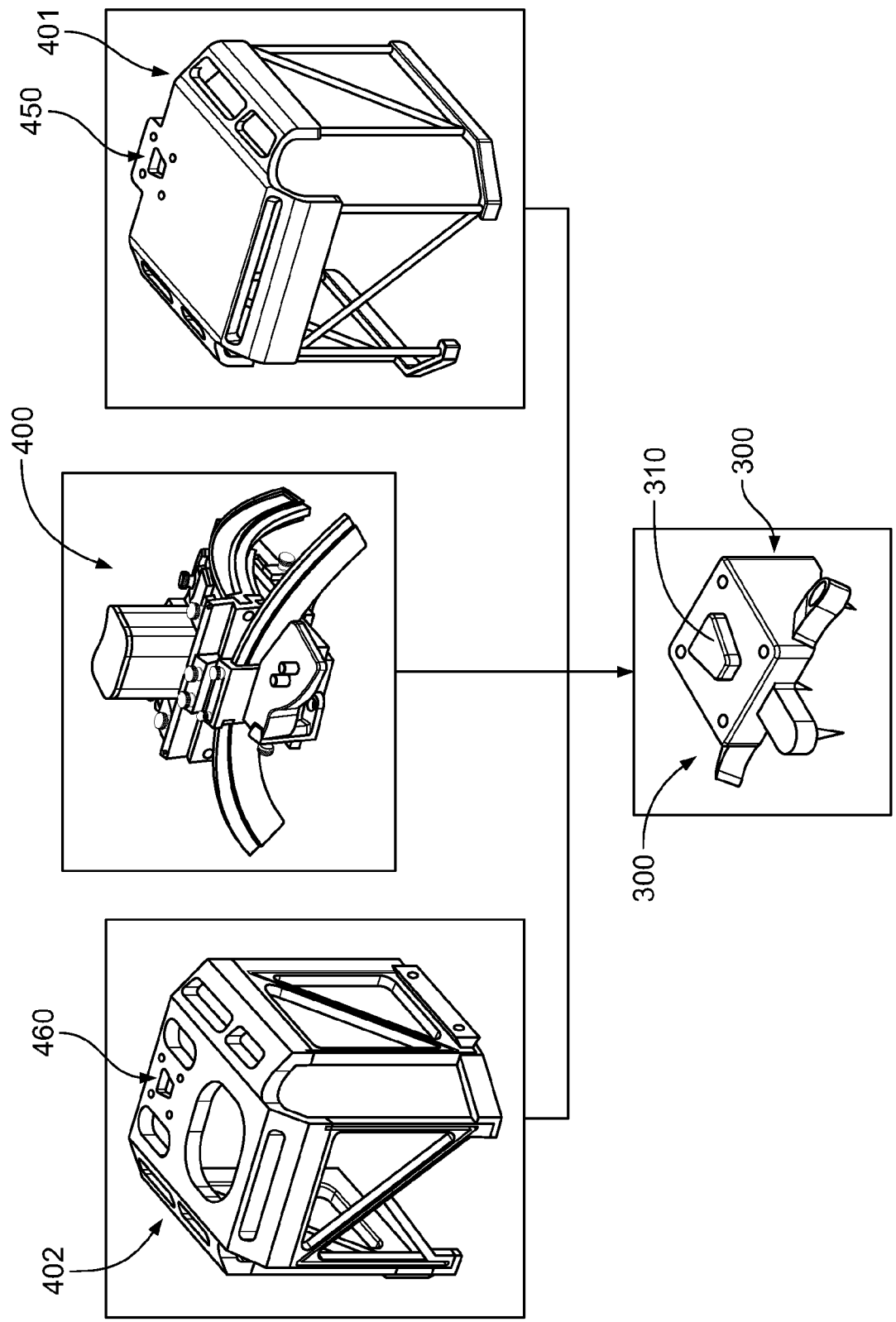
FIG. 41 illustrates various stereotactic devices that are designed to mate with the skull attachment device of FIGS. 34-38.
Figure 43:
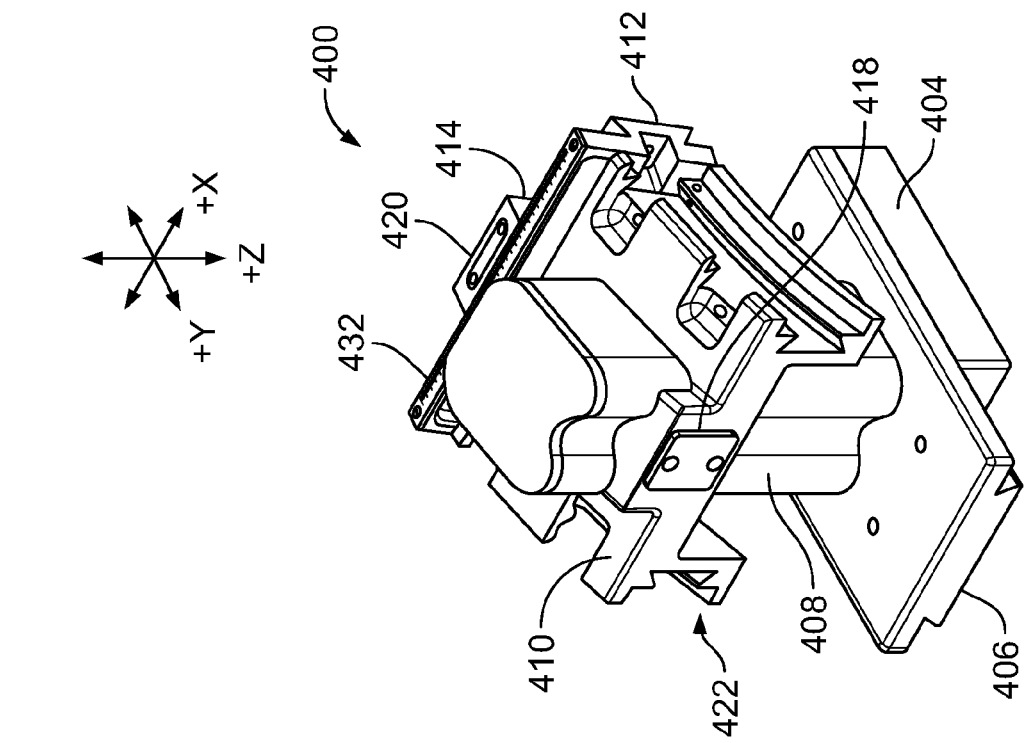
FIGS. 42 and 43 illustrate various views of a portion of a stereotactic positioning device that is designed to mate with the skull attachment device of FIG. 34.
Figure 42:
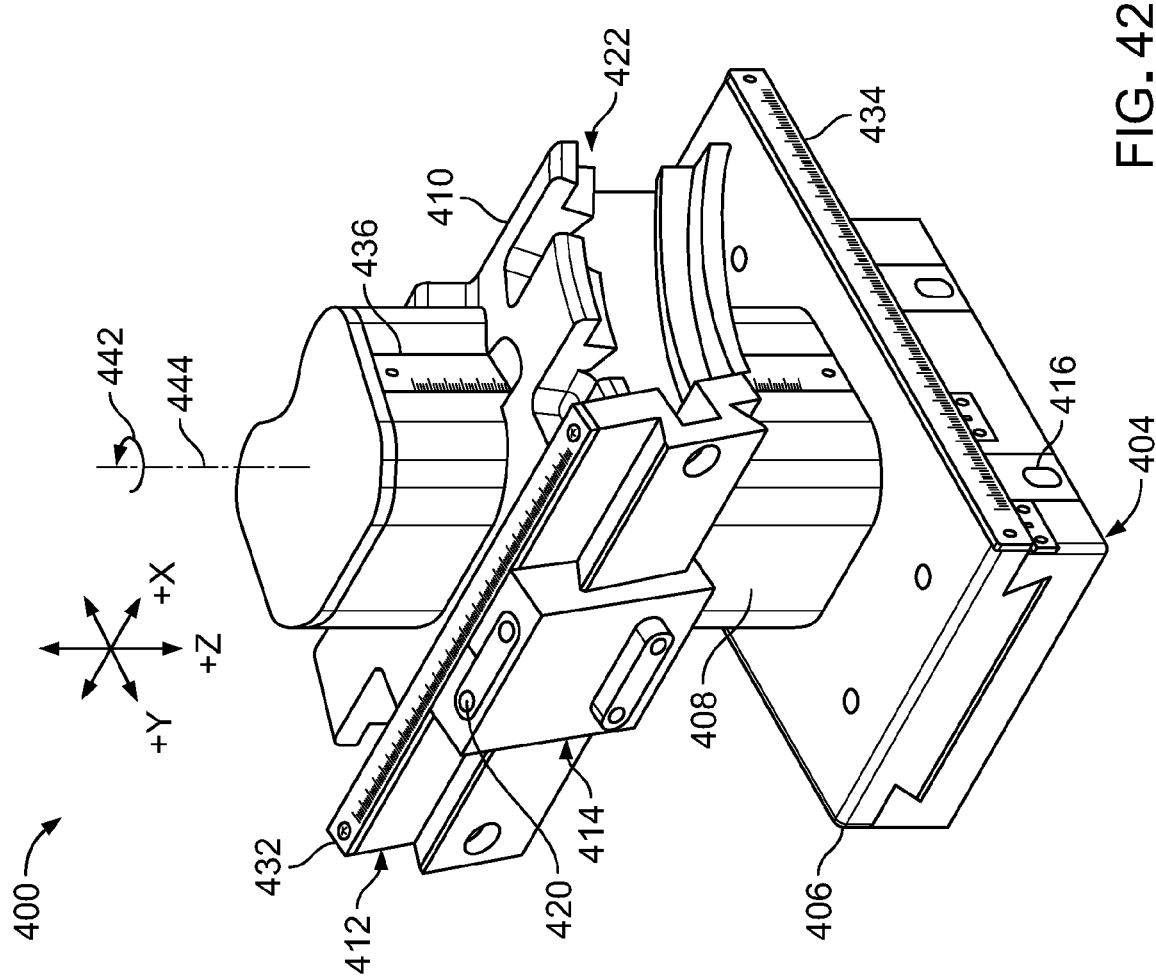

Referring to FIG. 41, multiple cooperating stereotactic devices can be attached to the skull attachment device 300 in an identical manner. Example devices include a stereotactic positioning device 400, a CT image localizer 401, and an MRI localizer 402 that respectively have a mating feature (e.g., a receptacle) 430, 450, 460 that is formed complimentary to the interface 310. (In some cases, the stereotactic positioning device 400 may also be referred to as a stereotaxic positioning device.) This interchangeability provides the capability of removing a cooperating stereotactic device from an original position along the skull 301 and subsequently relocating the same or different cooperating stereotactic device to the original position at a desired time as long as the skull attachment device 300 remains secured to the skull 301. Accordingly, a stereotactic surgery and acquisition of a CT scan or MRI scan can be performed on different days. Each of the devices 400, 401, 402 includes a mating feature (e.g., a receptacle, pocket, or recessed profile) of identical dimensions, such that each of the devices 400, 401, 402 aligns with the interface 310 of the skull attachment device 300 in the same manner and at the same position of the stereotactic coordinate system defined by the skull attachment device 300.

As discussed above, stereotactic deep drain stimulation (DBS) surgery is an arduous experience for patients. Implantation of a DBS system is staged into two separated procedures. During the first stage, one or more DBS leads are implanted over 2-3 hours and is performed on a patient that is awake because feedback from the patient is essential in order to optimize placement of the DBS leads. The second stage, typically perform on a second day, includes implantation of a DBS stimulator and connecting the DBS leads to the DBS stimulator. The second stage takes 1-2 hours and is performed with the patient being under general anesthesia.

As discussed above with respect to the template 2, in some implementations, a workflow to implant DBS leads begins in an operating room (OR), and a stereotactic system is attach to the patient's skull with a headframe that is secured in place using four sharply pointed screws. A surgeon tightens the screws, driving the points into the outer table of the skull. Patients often consider this the worst part of the procedure, as the pressure from the sharp screws creates an enduring ache until the headframe is removed at the end of the procedure.

Referring to FIGS. 42-48, the stereotactic positioning device 400 is designed to address several drawbacks of other stereotactic DBS procedures, including discomfort created by a headframe, weight of conventional stereotactic devices, and the length of DBS surgery. The stereotactic positioning device 400 significantly differs from other stereotactic devices in that the stereotactic positioning device 400 is designed to attach to the skull attachment device 300 for immobilizing a patient's head instead of a conventional headframe. The stereotactic positioning device 400 is a light weight, re-locatable instrument guide that is able to deliver a variety of instruments to intracranial targets to perform procedures such as DBS, stereotactic biopsies, stereotactic intraventricular shunt placement, and placement of extra ventricular drains (EVD). In some embodiments, performing a DBS procedure using the skull attachment device 300 and the stereotactic positioning device 400 may require only one person and about one to two hours of time, as compared to a requisite of two persons and a time of about four to five hours when performed using conventional stereotactic devices.

Figure 49:
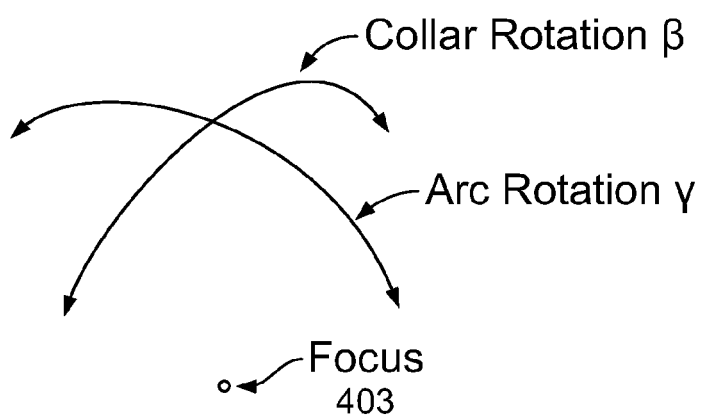
FIG. 49 illustrates collar and arc angular rotations of the stereotactic positioning device of FIGS. 42-47.

Referring to FIG. 49, the stereotactic positioning device 400 is an arc-centered stereotactic device. That is, the stereotactic positioning device 400 has three linear degrees of freedom (e.g., X, Y, and Z) and two rotational degrees of freedom that include a collar angle β and an arc angle γ. The rotational degrees of freedom are oriented at 90 degrees from each other (e.g., the rotational degrees of freedom are orthogonal to each other). The arc and collar angles β, γ rotate about a single point called a focus 403. The combined rotations define a sphere in space that is centered at the focus 403. Biopsy instruments, DBS leads, shunts, and EVD drains are held along a normal vector of this sphere, directing these components to the focus 403. The surgical target within the brain is positioned at the focus 403, and an instrument may be accurately, mechanically placed at the focus 403 within a tolerance of about 0.5 mm using the stereotactic positioning device 400. Additionally, an error of the system includes errors induced by limitations of imaging and is about 1.8 mm.

The function of the stereotactic positioning device 400 is to move the focus 403 (e.g., corresponding to a surgical target within the brain) in directions of left/right (X), anterior/posterior (Y), and inferior/superior (Z). A position along each axis is derived from stereotactic surgical planning software that outputs X, Y, and X coordinates to the surgical target. Accordingly, and referring particularly to FIGS. 42 and 43, the stereotactic positioning device 400 includes a Y axis rail 404, a Y axis carrier 406 that is movable linearly along the Y axis rail 404, a Z axis rail 408 that extends from the Y axis carrier 406, a Z axis carrier 410 that is movable linearly along the Z axis rail 408, an X axis rail 412, and an X axis carrier 414 that is movable linearly along the X axis rail 412.

The stereotactic positioning device 400 also includes a Y axis break 416 that locks the position of the Y axis carrier 406 along the Y axis rail 404, a Z axis break 418 that locks the position of the Z axis carrier 410 along the Z axis rail 408, and an X axis break 420 that locks the position of the X axis carrier 414 along the X axis rail 412. The Y axis carrier 406 can typically move a distance of up to about 70 mm along the Y axis rail 404. The X axis carrier 414 can typically move a distance of up to about 70 mm along the X axis rail 412. The Z axis carrier 410 can typically move a distance of up to about 80 mm along the Z axis rail 408. Each of the X, Y, and Z axis rails 412, 404, 408 also has a respective ruler 432, 434, 436 with a metric scale (e.g., millimeters) and corresponding tic marks. The positions of the carriers 406, 410, 414 are adjusted to match the output coordinates of the surgical target, which places the focus 303 at the surgical target.

Figure 44:
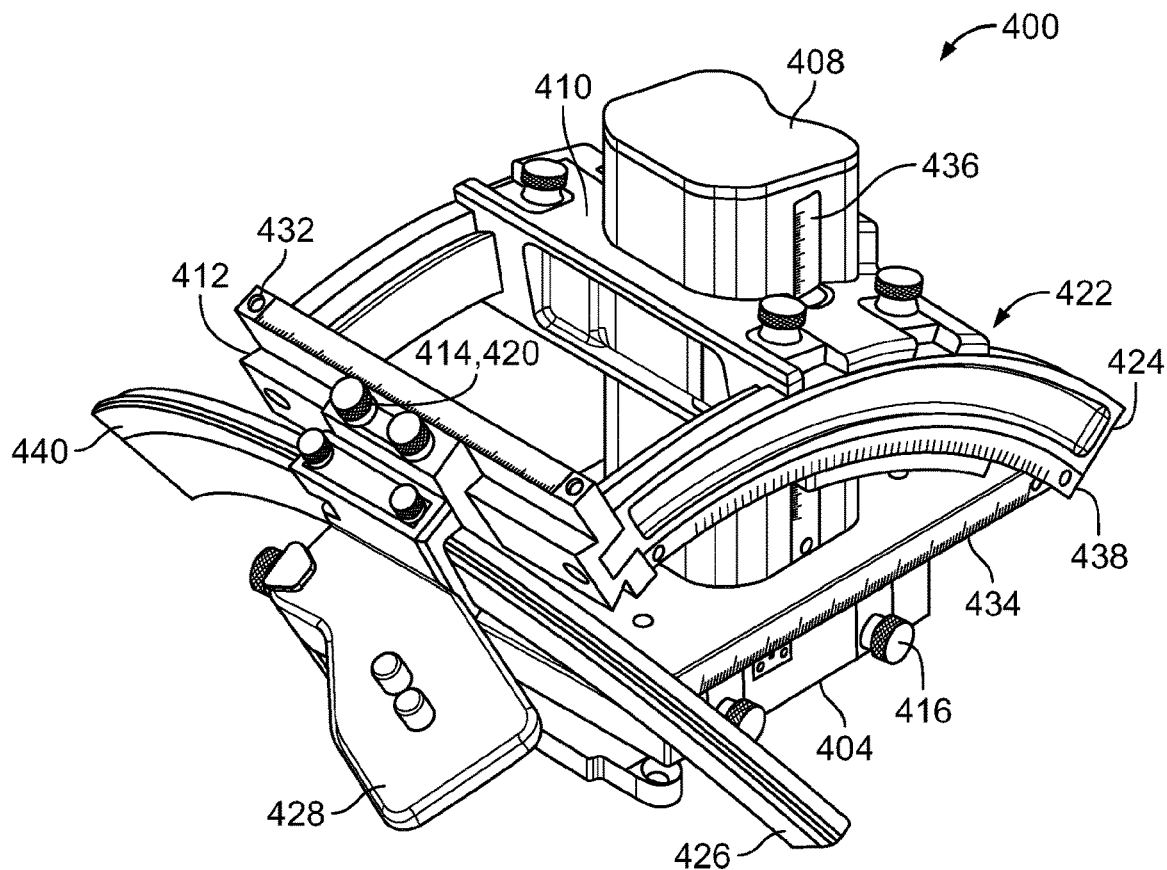
FIGS. 44-47 illustrate various additional views of the stereotactic positioning device of FIGS. 42 and 43.
Figure 45:
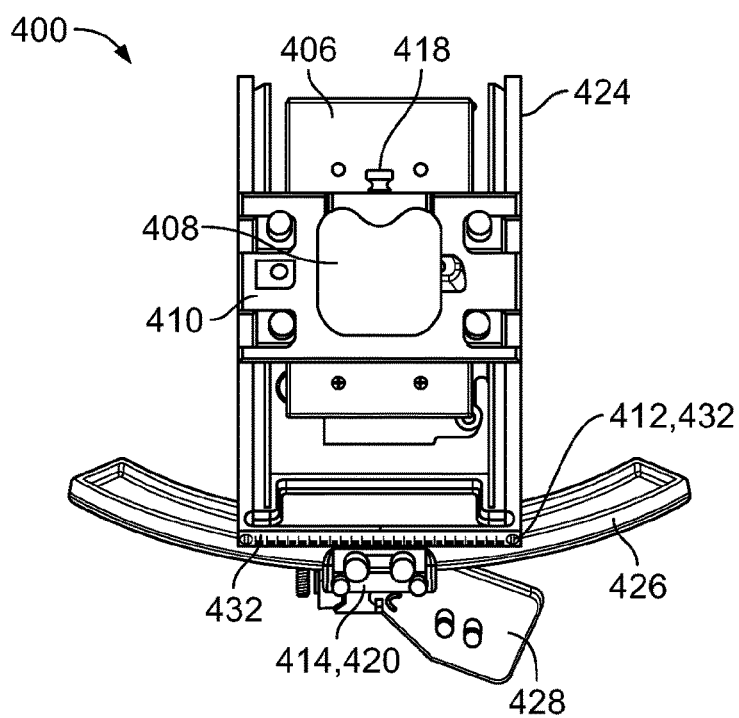
Figure 46:
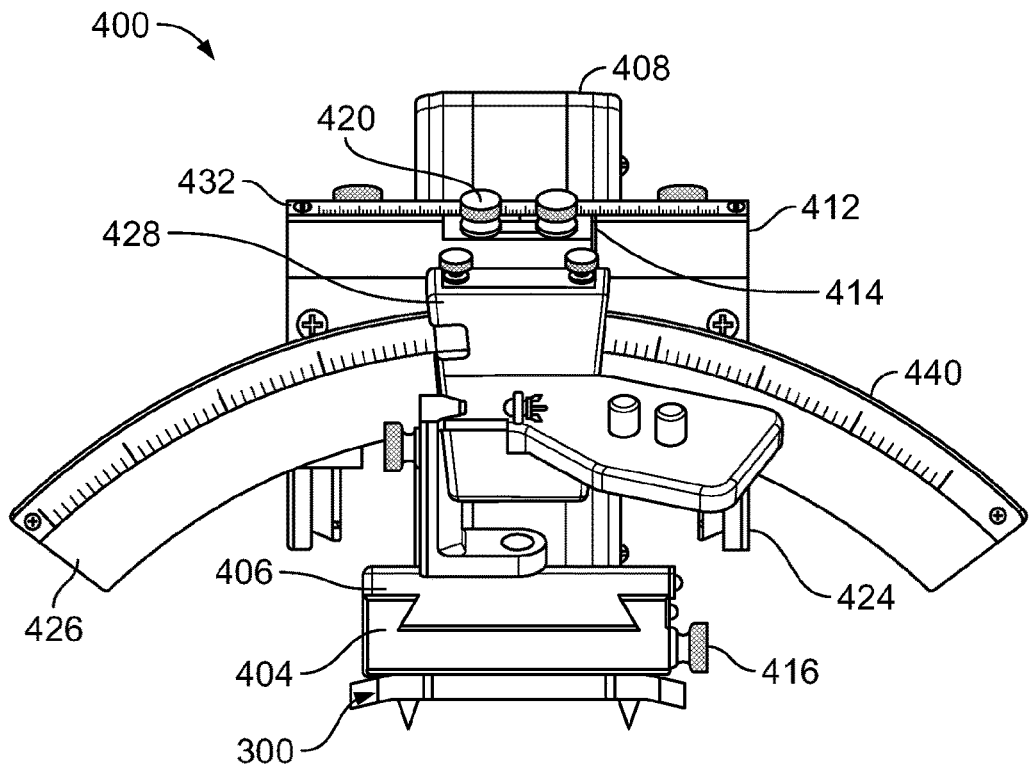
Figure 47:
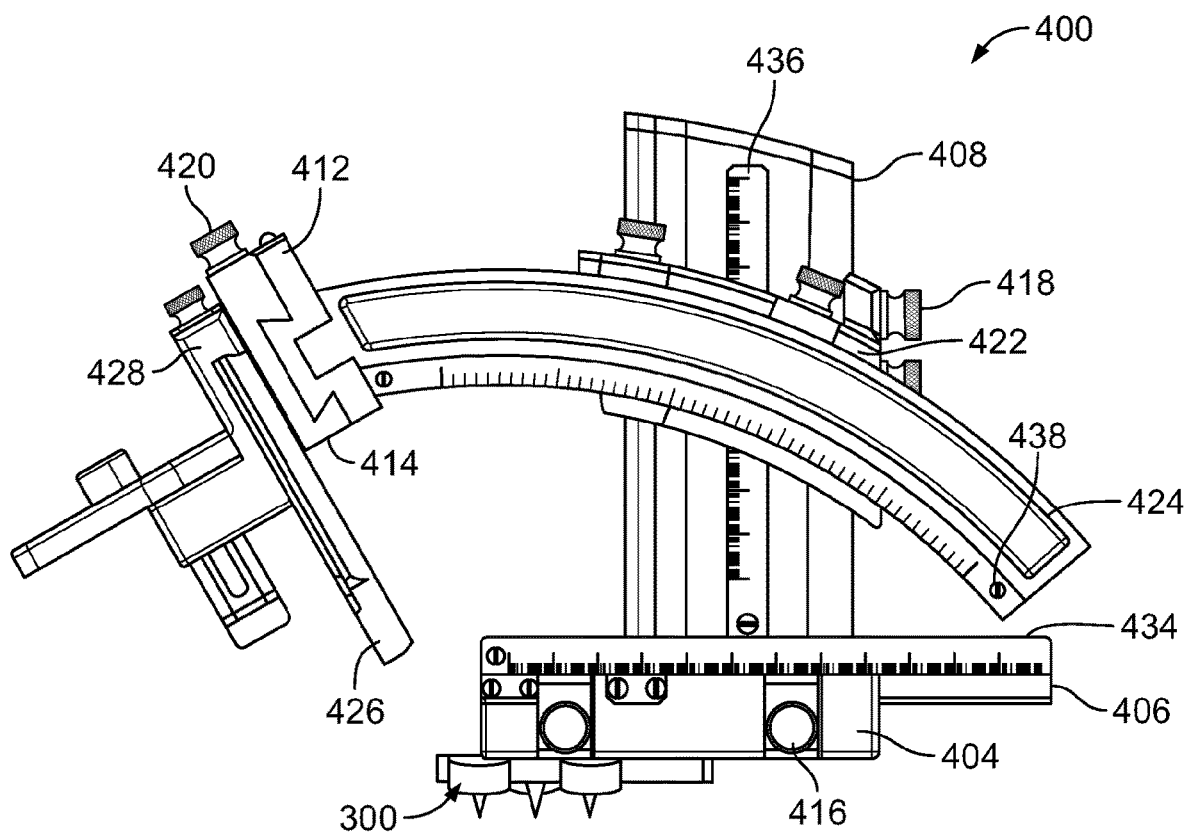

Referring particularly to FIGS. 44 and 49, the stereotactic positioning device 400 further includes two opposing curved collar rails 422 that are defined by the Z axis carrier 410 and two opposing collar carriers 424 that are movable angularly along the collar carriers 422 to vary the collar angle β (e.g., to vary the anterior/posterior tilt of the X axis carrier 414). The X axis rail 412 is mounted to ends of the collar carriers 424. The stereotactic positioning device 400 further includes a curved arc rail 426 that is carried by the X axis carrier 414 and an arc carrier 428 that is movable angularly along the arc rail 426 to vary the arc angle γ (e.g., to vary the left/right tilt of the arc carrier 428). The collar and arc carriers respectively have curved rulers 438, 440 with metric scales (e.g., millimeters) and corresponding tick marks.

Accordingly, the collar angle β provides rotation about the X axis passing through the focus 303, and the arc angle γ provides rotation about the Y axis passing through the focus 303. The collar rails 422 typically have a radius of curvature of about 170 mm to about 180 mm (e.g., about 172.7 mm), which is much larger than conventional mechanical pivot rings in the field with radii of about 50 mm. The collar rails 422 typically extend over an angle β of about 30 degrees to about 80 degrees and typically have an arc length of about 190 mm to about 200 mm (e.g., about 194 mm). The arc rail 426 typically has a radius of curvature of about 160 mm to about 170 mm (e.g., about 165 mm), typically has an arc length of about 280 mm to about 290 mm (e.g., about 284.9 mm), and typically extends over an angle γ of about +/−50 degrees with respect to a center of the X axis carrier 414. This design allows for a more compact unit because the collar carriers 424 are located above the patient's head. Attachment of the arc rail 426 and the arc carrier 428 directly to the X axis carrier 424 also contributes to the compact design.

In some embodiments, the stereotactic positioning device 400 also provides for rotation (refer to arrow 442) about the Z axis. For example, the Z axis rail 408 may be rotatable about its axis 444 and with respect to the Y axis carrier 406 from which the Z axis rail 408 extends. The addition of this articulation expands the flexibility of a trajectory to the target, thereby optimizing a safe trajectory to the target.

In some embodiments, the stereotactic positioning device 400 may be made of one or more materials, including POM, aluminum, and polycarbonate. The stereotactic positioning device 400 has a compact footprint (e.g., excluding the collar carrier 424 and the arc rail 426) that typically has a length of about 125 mm to about 165 mm (e.g., about 140 mm), a width of about 110 mm to about 120 mm (e.g., about 114.3 mm), and a height of about 135 mm to about 150 mm (e.g., about 142.6 mm). The stereotactic positioning device 400 typically has a total weight about 1100 g to about 2000 g.

Various microdrive units and delivery systems may be secured to the arc carrier 428 to carry out a surgical procedure at the focus 303 of the arc quadrant (e.g., defined by the collar rail 422, the arc rail 426, and the arc carrier 428) within the patient's head. As discussed above with respect to FIG. 40, the origin of the stereotactic coordinate system is located to the right, posterior, superior corner of the skull attachment device 300, such that a center of the work envelope 322 is defined to a center of the patient's head (X=100, Y=100, Z=100). In contrast, the origin of conventional arc-centered stereotactic devices is the center of the work envelope. In some embodiments, the stereotactic positioning device 400 can emulate these systems by designing the X, Y, and Z scales to place the origin (0,0,0) at the center of the scales. The ability to change the scales to match other commercially available systems enables the use of corresponding surgical planning software to plan surgical targets. The work envelope 322 typically has a length (e.g., along the X axis) of about 75 mm to about 95 mm (e.g., about 80 mm), a width (e.g., along the Y axis) of about 55 mm to about 90 mm (e.g., about 60 mm), and a height (e.g., along the Z axis) of about 50 mm to about 90 mm (e.g., about 70 mm)

Figure 48:
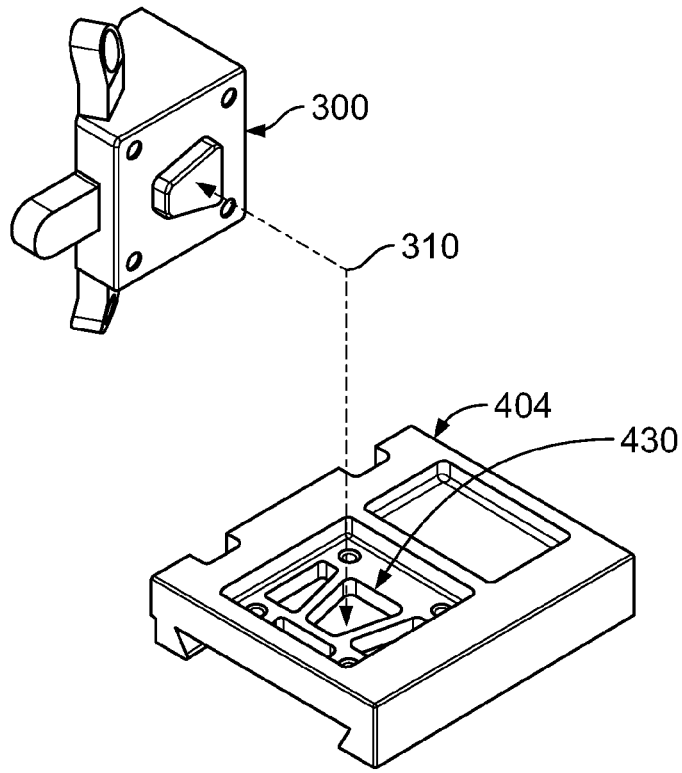
FIG. 48 illustrates a portion of the stereotactic positioning device of FIGS. 42-47 that includes a mating feature for interfacing with the skull attachment device of FIGS. 34-38.

Referring to FIG. 48, the Y axis carrier 406 defines a receptacle 430 that is designed to mate with the interface 310 of the skull attachment device 300 to accurately position the stereotactic positioning device 400 with respect to the skull 301. Accordingly, the receptacle 430 has a geometry that is complimentary to that of the interface 310.

Regarding image localization and surgical planning, and as discussed above, the CT image localizer 401 and the MRI localizer 402 are designed to be attached to the skull attachment device 300, which maintains the localizers 401, 402 in a specific location and orientation for the stereotactic coordinate system. Images generated with the localizers 401, 402 typically have 9-12 reference marks (e.g., fiducials) that are used to quantify the location of an image in stereotactic space. These images are input into surgical planning computers that locate each fiducial on every image. The software uses the fiducials to create a transformation matrix that allows a translation from image space to stereotactic space.

A stereotactic system including the localizers 401, 402 and the stereotactic positioning device 400 is designed to function with conventional stereotactic planning software packages. This is possible by emulating the physical dimensions of various image localizers and matching XYZ values of the stereotactic coordinate system discussed above to that of XYZ scales of the various image localizers. This allows a surgeon to continue using his or her preferred stereotactic planning software with the stereotactic system.

Surgical planning programs allow the surgeon to simulate a stereotactic device using MRI or CT image volumes. The surgeon locates the desired target in the image volume and selects that pixel as the target point. The software outputs an XYZ coordinate ($X_T, Y_T, Z_T$) for that point. Additionally, the software allows the surgeon to simulate a trajectory from the surface of the brain to the target. The surgeon reviews and alters the trajectory until a safe path is plotted. The software output for this trajectory provides the values for the arc (A) and collar (C) angles. The completed surgical plan contains the values $X_T, Y_T, Z_T$, A, and C.

Figure 50:
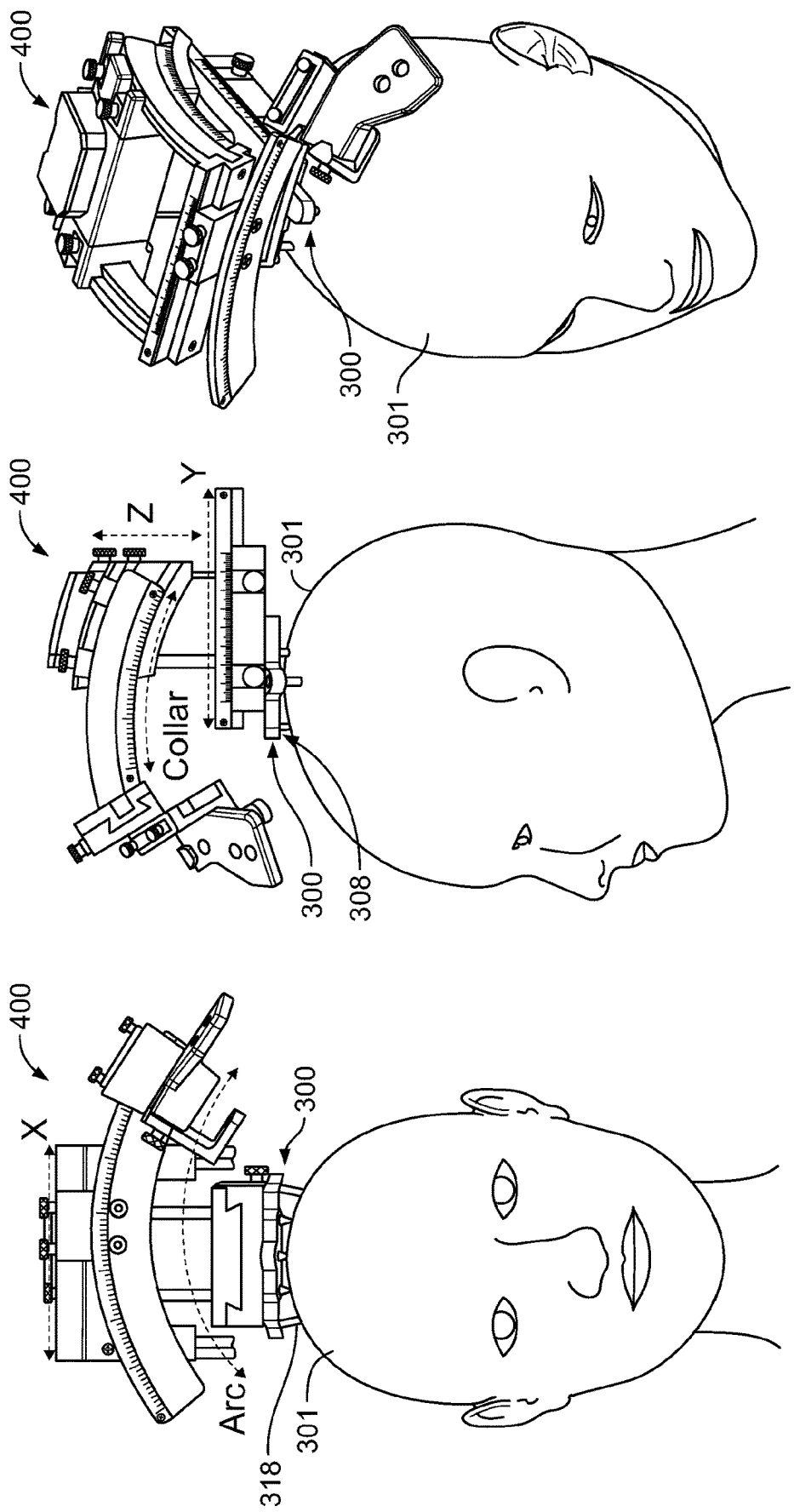
FIG. 50 illustrates various views of the stereotactic positioning device of FIGS. 42-47 as secured to a skull via the skull attachment device of FIGS. 34-38 for surgical planning.

Any time after the completion of the stereotactic planning (e.g., the same day or a subsequent day), the patient is taken to the OR, with the skull attachment device 300 still secured to the skull 301 in its original position. The patient is positioned on the OR table, and the surgical field is prepped for surgery. Referring to FIG. 50, a sterile stereotactic positioning device 400 is attached to the skull attachment device 300. The X, Y, and Z axis carriers 414, 406, 410 are set to the coordinate ($X_T, Y_T, Z_T$) of the surgical target. Each carrier 414, 406, 410 is translated until the value on the rulers 432, 434, 436 at which the carriers 414, 406, 410 are positioned match those of the surgical software output. As discussed above, the collar and arc angles β, γ define the surgical trajectory. The collar and arc rulers 438, 440 have scales engraved in 1° increments. The collar and arc carriers 424, 428 are adjusted to match the output of the stereotactic planning software.

Figure 51:
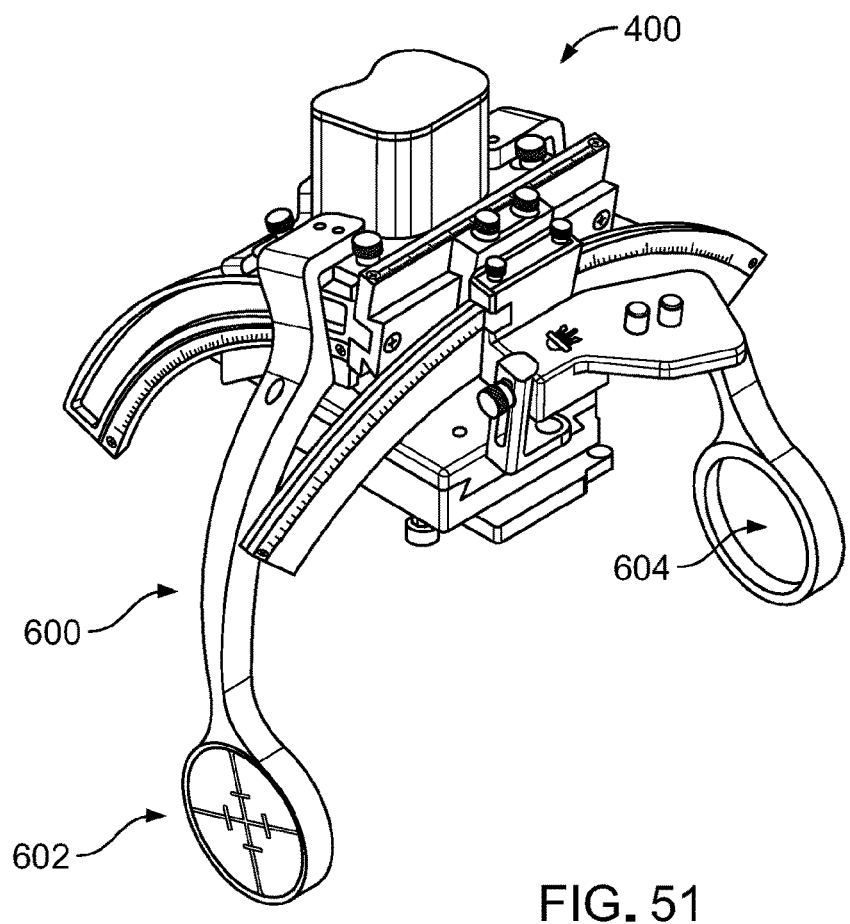
FIG. 51 illustrates an imaging reference tool attached to the stereotactic positioning device of FIGS. 42-47.
Figure 52:
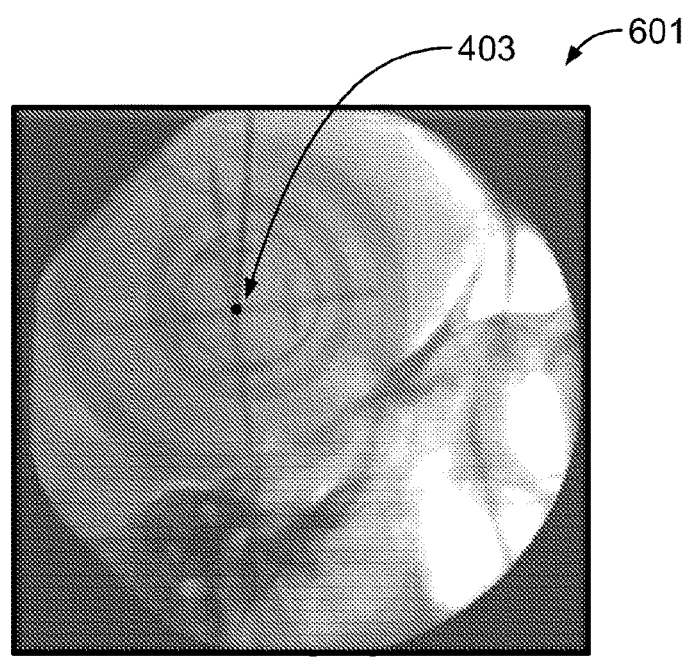
FIG. 52 illustrates a lateral x-ray of a reticle and corresponding circle of the imaging reference tool.

Referring to FIGS. 51 and 52, after a delivery system is secured to the arc carrier 428 and used to position a DBS lead in position in the patient's brain, a lateral x-ray 601 is obtained to confirm that the lead is indeed at the focus 403 of the arc quadrant. An imaging reference tool 600 is attached to the Z axis carrier 410. The imaging reference tool 600 includes a cross-hair reticle 602 on one side of the stereotactic positioning device 400 (e.g., on one side of the patient's head) and includes a corresponding circle reticle 604 on the opposite side. Superimposition of the cross-hair reticle 602 and the circle 604 indicates proper alignment of the reticles 602, 604 with the x-ray machine. Once aligned, the center of the cross-hair reticle 602 indicates the location of the focus 403 of the arc-quadrant, as shown in FIG. 52. The DBS lead (e.g., or any instrument) directed by the arc quadrant will project a path to the focus 403. The lateral x-ray 601 verifies that proper positioning is achieved in the arc-quadrant.

A number of embodiments have been described. Nevertheless, it will be understood that various modifications may be made without departing from the spirit and scope of the present disclosure. For example, while the various stereotactic components discussed herein have been described with respect to certain dimensions, operational parameters, material constituencies, and shapes, in some embodiments, stereotactic components that are generally similar in construction and function to the those described above may include different dimensions, operational parameters, material constituencies, and shapes.

In another example, a skull attachment device that is similar to the skull attachment device 300 may be adapted for use with the stereotactic device 200. For example, in lieu of using screws to secure the robotic device, the base platform of the robotic device may be adapted to interface with the skull attachment device 300.

Figure 53:
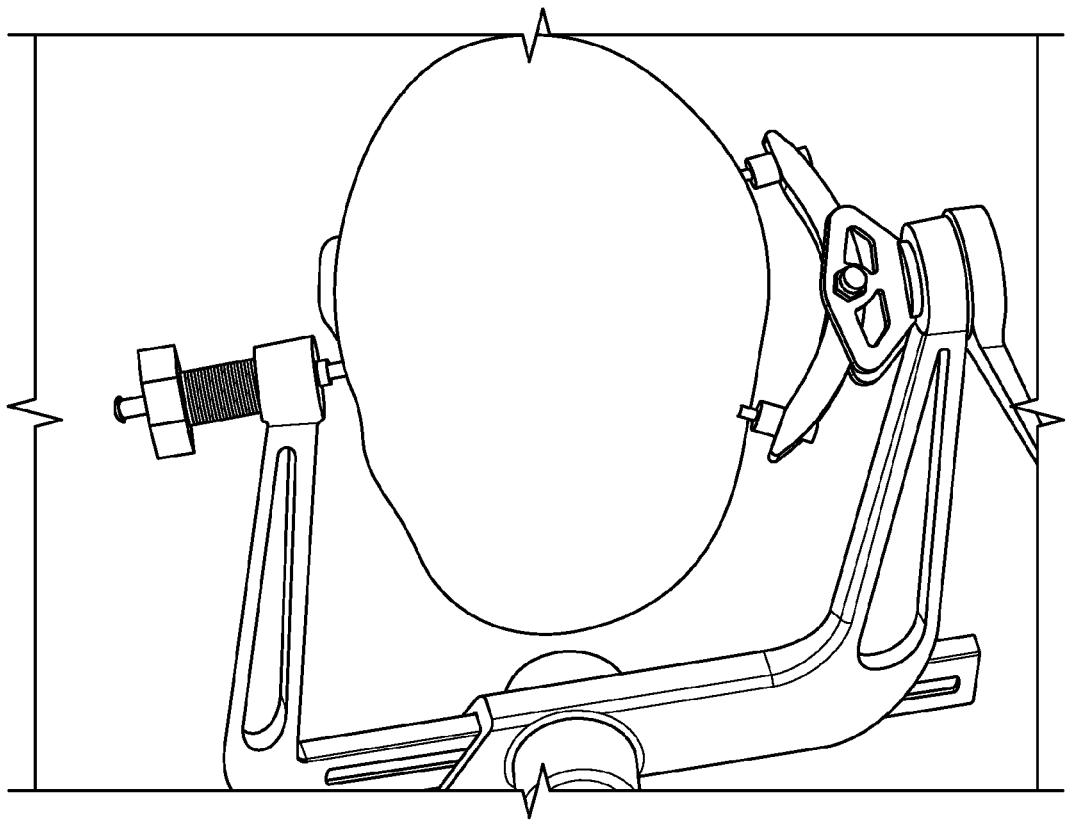
FIG. 53 illustrates pinion attachment of a skull attachment device to a skull.

In some embodiments, a skull attachment device that is otherwise similar in construction and function to the skull attachment device 300 may be alternatively secured to a skull with two arms having sharp pins that imbed into the skull, as shown in FIG. 53.

Figure 54:
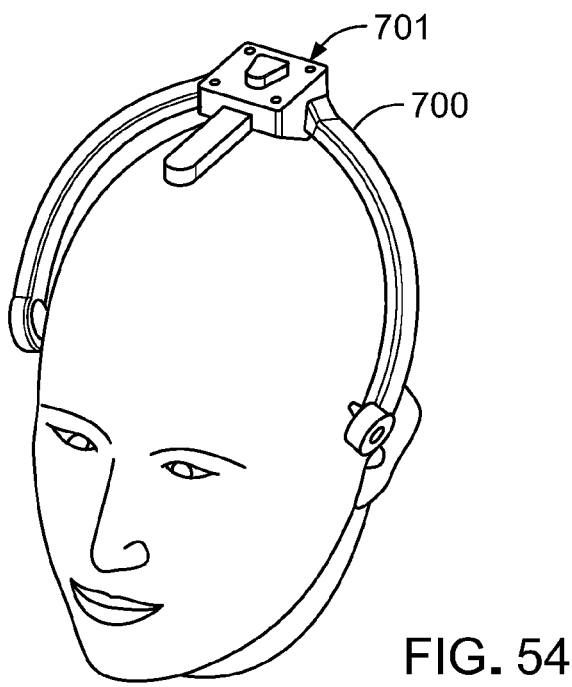
Figure 60A:
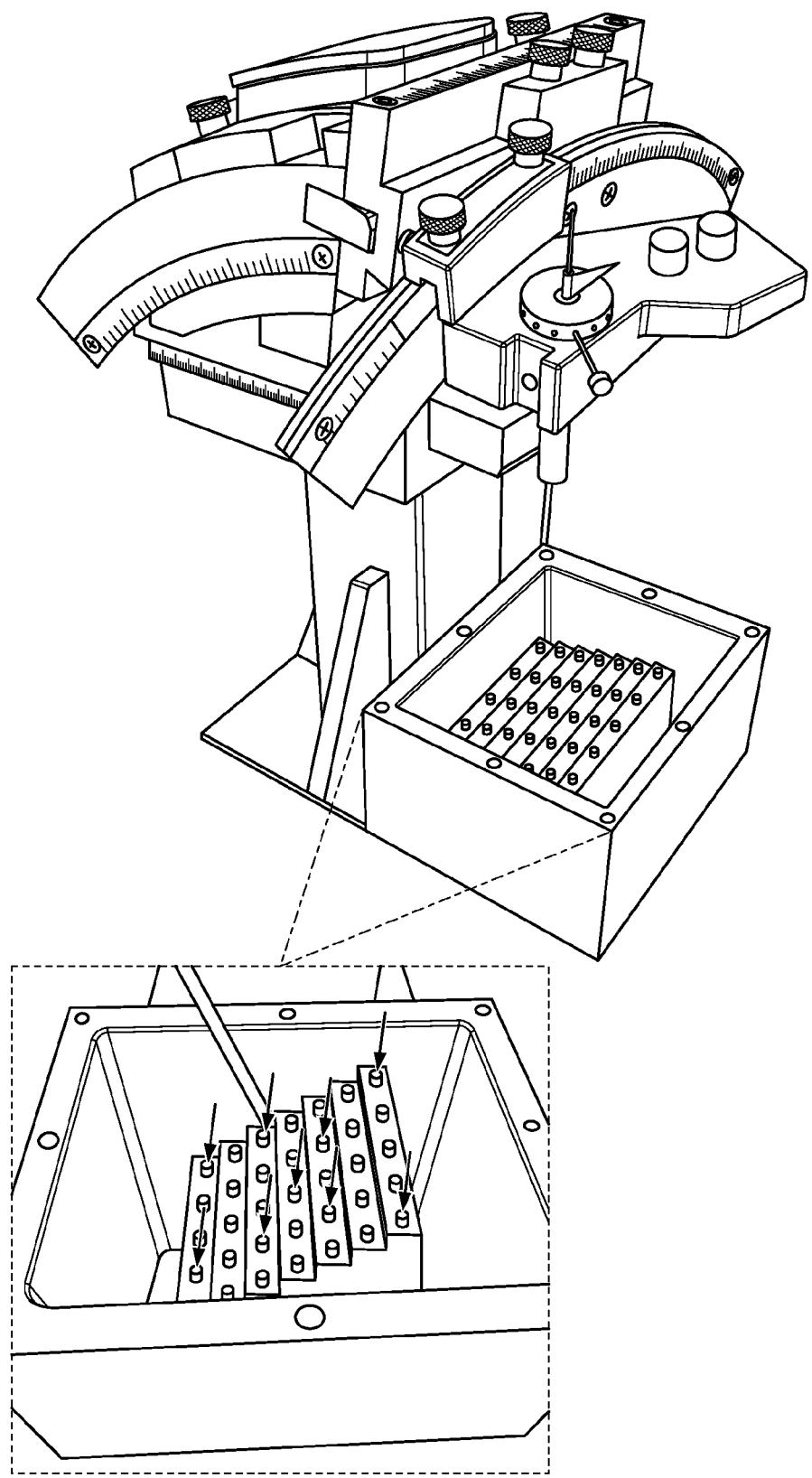
FIG. 60A-60D illustrates phantom testing performed with the stereotactic positioning device of FIGS. 42-47.
Figure 60B:
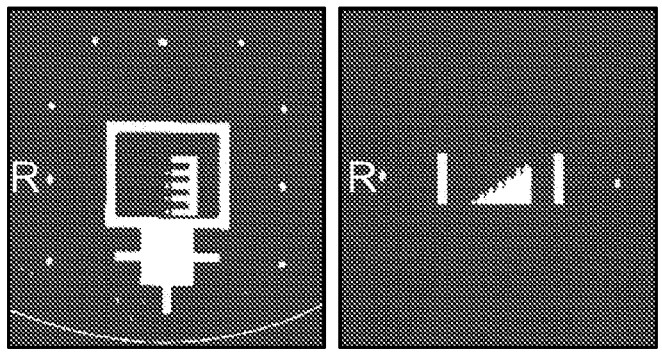
Figure 60C:
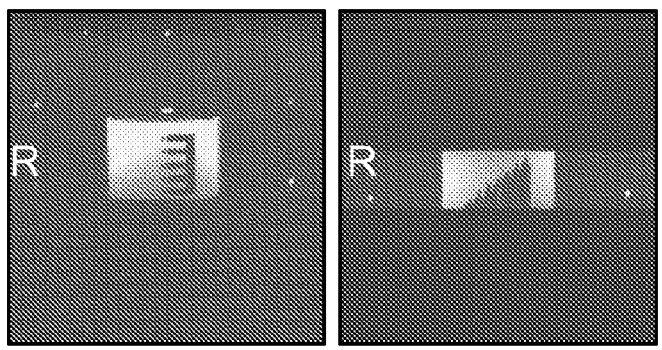
Figure 60D:
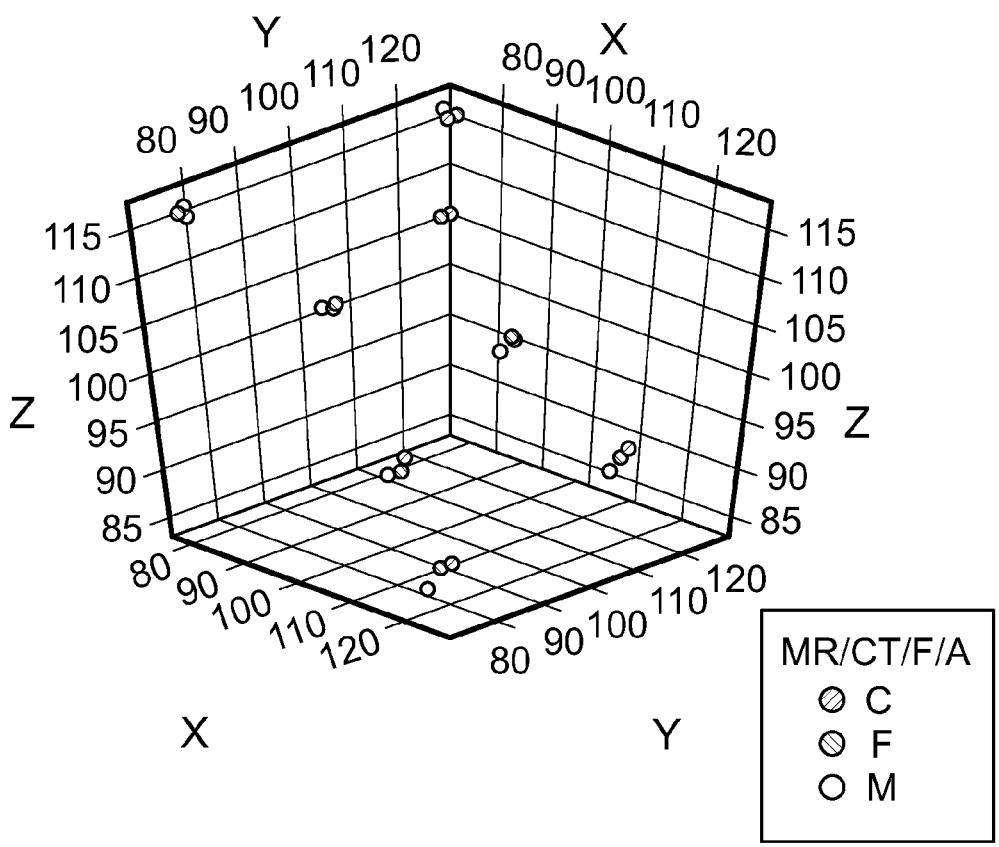
Figure 61A:
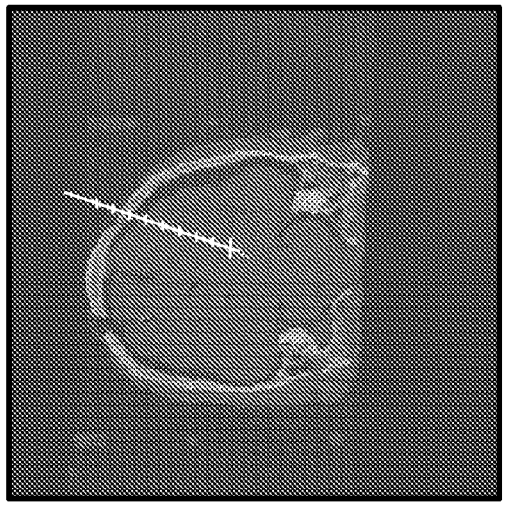
FIG. 61A-61F illustrates CT images demonstrating bilateral targeting accuracy achieved using the stereotactic positioning device of FIGS. 42-47.
Figure 61B:
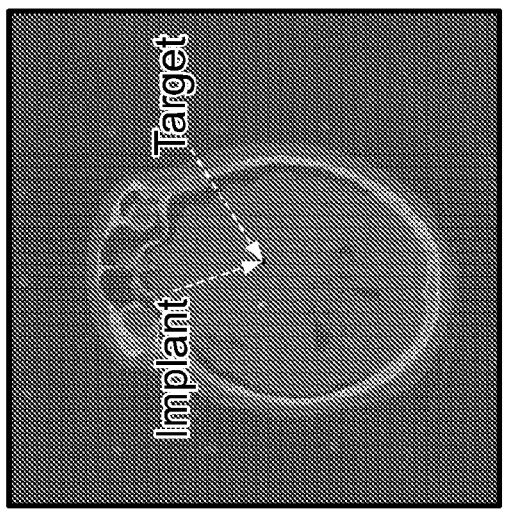
Figure 61C:
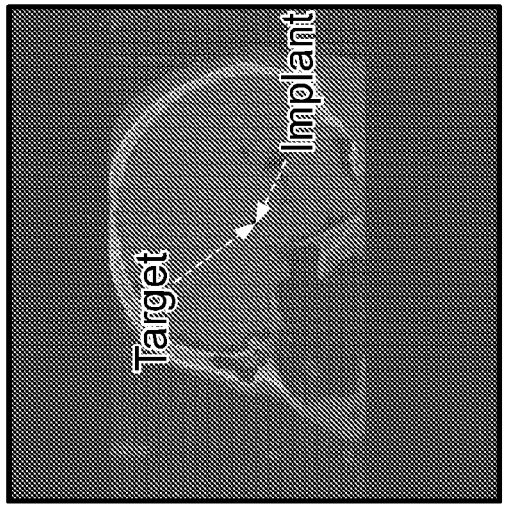
Figure 61D:
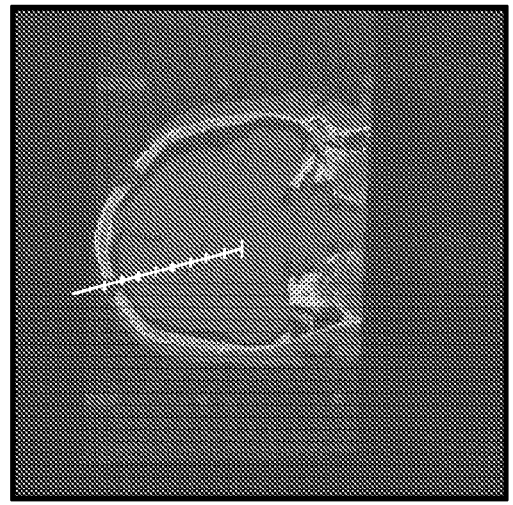
Figure 61E:
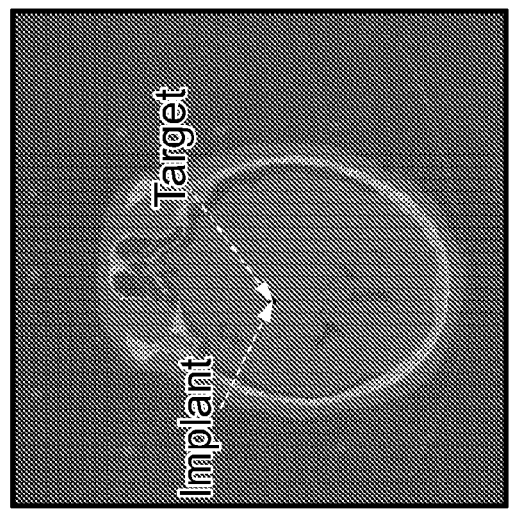
Figure 61F:
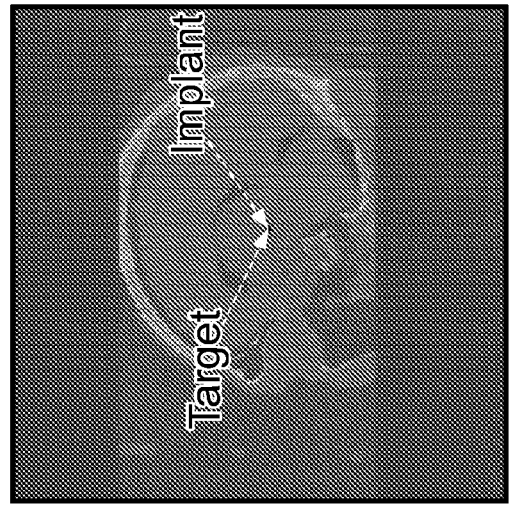

FIG. 54 illustrates several components by which skull attachment devices that are similar in construction and function to the skull attachment device 300 may be alternatively anchored to a patient's skull. In FIG. 54, arms 700 extend to either side of the patients head, and sharp pointed screws are driven into the skull to anchor a skull attachment device 701. In FIG. 55, arms 702 of a skull attachment device 703 are mounted to a hinge 704. Adjusting screws 705 drive the arms 702 toward the center, driving sharp pins 706 into the skull. The skull attachment device 707 in FIG. 56 is similar in design to the skull attachment device 701, with the addition of a cross brace 708 on the posterior side of the head. FIGS. 57 and 58 illustrate a skull attachment device 709 that is similar to the skull attachment device 707, except that the number of anchor screws 711 is reduced to one, making application easier. FIG. 59 illustrates a ratchet 710 that allows a user to drive a sharp pin into the skull to anchor a skull attachment device.

Referring to FIG. 60, the stereotactic system 400 was attached to a custom MRI/CT-compatible phantom with 35 potential targets of known coordinate (A). The mechanical accuracy was evaluated by adjusting the stereotactic frame system to target 9 phantom points (A). To demonstrate repeatability, three independent users repeated frame targeting across three separate trials. The root mean square error (RMSE) between the ground truth image locations and the frame-targeted coordinates calculated across the 9 points was 1.59 mm (n=4 individuals). A stereotactic surgical planning software was used to target each phantom point in image space and provide stereotactic coordinates. The RMSE between the frame-targeted and the CT- and MM-targeted coordinates was 1.72 mm and 1.79 mm, respectively. For visualization purposes, the ground truth locations of the 9 phantom points are plotted in 3-D stereotactic space, with the average frame-targeted, CT-targeted, and MRI-targeted coordinates (C). To examine the system's ability to remain accurate at different collar and arc angles, an additional experiment was performed to assess the ability of the system to hit one of 8 phantom points as the arc and collar angles increased by 10° increments. The average Euclidean distance for different arc and collar angles was found to be 0.82 mm and 0.67 mm respectively (N=3 individual, refer to FIG. 54).

FIG. 61 shows the pre-surgical plan overlaid onto a post-operative CT, demonstrating the accurate placement of the DBS electrode to the planned target. Eight DBS implantations were conducted on 3 cadaveric specimens to examine the ability to secure to heads of different size and to examine the repeatability of placement across different specimens using the stereotactic positioning device 400. The average TLE was 1.9 mm±0.4 (n=7 implantations, 3 cadavers, ±SD). Frame 001 was used for experiments 1, 2 and Frame 002 was used for experiments 3-8. The average target localization error for Frame 001 was 1.95 mm (1.82-2.07 mm), and for Frame 002 was 1.90 mm±0.48 (1.13-2.53 mm). One of the 8 implantations was excluded from the calculation, as this electrode followed an accurate trajectory but was inserted 5 mm too deep due to a malfunction in an anchor, a common clinical occurrence. The 3D Euclidian distance of the second electrode contact to the target was found to be 0.58 mm but was 5.2 mm from distal portion of the first electrode contact.

Additionally, while the template 2, the various anchor screws and standoffs, and the stereotactic devices 100, 200 have been illustrated and described as having certain dimensions, operational parameters, material constituencies, and shapes, in some embodiments, templates, screws, and standoffs that are generally similar in construction and function to the those described above may include different dimensions, operational parameters, material constituencies, and shapes. Other embodiments are within the scope of the following claims.

What is claimed is:

1. A surgical system, comprising:
a stereotactic device; and
a skull attachment device comprising: a support base configured to seat against a skull of a patient;
one or more pins extending from a bottom surface of the support base and configured to pierce a scalp to seat the skull attachment device against the skull; and
an interface disposed along a top surface of the support base and having a shape that compliments a profile of a mating feature of the stereotactic device for defining a position and an orientation of the stereotactic device with respect to the support base while the interface is engaged with the mating feature,
wherein the top surface of the support base defines a plane comprising an origin of a stereotactic coordinate system while the skull attachment device is seated against the skull,
wherein the stereotactic device comprises an instrument guide,
wherein the stereotactic device is adjustable in three linear degrees of freedom and is adjustable in two or more rotational degrees of freedom for guiding an instrument to a target point located in a brain of the patient,
wherein the stereotactic device comprises an X axis carrier that is movable along an X axis rail, a Y axis carrier that is movable along a Y axis rail, a Z axis carrier that is movable along a Z axis rail, a collar angle carrier that is movable along a collar angle rail, and an arc angle carrier that is movable along an arc angle rail, and
wherein the collar angle carrier and the arc angle carrier together define a sphere having a center point that is configured to be coincident with the target point in the brain of the patient.

2. The surgical system of claim 1, wherein the top and bottom surfaces of the support base together define an angle in a range of about 0 degrees to about 40 degrees.

3. The surgical system of claim 1, wherein the skull attachment device further comprises lateral protrusions extending from the support base and respectively defining holes through which anchor screws can be passed to attach the skull attachment device to the skull.

4. The surgical system of claim 1, wherein the support base comprises one or more features at which the support base can be attached to the stereotactic device.

5. The surgical system of claim 1, wherein the interface protrudes from the top surface of the support base.

6. The surgical system of claim 1, wherein the interface is radially asymmetric.

7. The surgical system of claim 1, wherein the stereotactic device comprises an image localizer.

8. The surgical system of claim 1, wherein the X axis rail is mounted to the collar angle carrier, and wherein the arc angle rail is mounted to the X axis carrier.

9. The surgical system of claim 1, wherein the collar angle carrier and the arc angle carrier are orthogonal to each other.

10. The surgical system of claim 1, wherein the collar angle rail has a radius of curvature of about 160 mm to about 190 mm, and wherein the arc angle rail has a radius of curvature of about 160 mm to about 190 mm.

11. The surgical system of claim 1, wherein the Z axis rail is rotatable about its own axis.

12. The surgical system of claim 1, further comprising an imaging reference tool configured to be attached to the stereotactic device for verifying accurate placement of the instrument at the target point.

13. The surgical system of claim 12, wherein the imaging reference tool comprises a cross-hair reticle and a circle disposed on opposite sides of the imaging reference tool.

14. The surgical system of claim 1, wherein the stereotactic device is a first stereotactic device and the mating feature is a first mating feature, the surgical system further comprising a second stereotactic device having a second mating feature with the profile of the first mating feature.

* * * * *

UNITED STATES PATENT AND TRADEMARK OFFICE
CERTIFICATE OF CORRECTION

| | | |
|---|---|---|
| PATENT NO. | : 12,059,312 B2 | Page 1 of 1 |
| APPLICATION NO. | : 16/966185 | |
| DATED | : August 13, 2024 | |
| INVENTOR(S) | : Kendall H. Lee and Stephan J. Goerss | |

It is certified that error appears in the above-identified patent and that said Letters Patent is hereby corrected as shown below:

In the Claims

In Column 18, Line 4, In Claim 1, delete "are angle" and insert -- arc angle --.

In Column 18, Line 4, In Claim 1, delete "are angle" and insert -- arc angle --.

Signed and Sealed this
Twenty-ninth Day of October, 2024

*Katherine Kelly Vidal*

Katherine Kelly Vidal
*Director of the United States Patent and Trademark Office*